US006436938B1

(12) United States Patent
Howard, Jr.

(10) Patent No.: US 6,436,938 B1
(45) Date of Patent: Aug. 20, 2002

(54) COMBINATION TREATMENT FOR DEPRESSION

(75) Inventor: Harry Ralph Howard, Jr., Bristol, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/973,614

(22) Filed: Oct. 9, 2001

Related U.S. Application Data

(60) Provisional application No. 60/263,278, filed on Jan. 22, 2001.

(51) Int. Cl.[7] .................. A61K 31/497; A61K 31/44; A61K 31/445; A61K 31/135
(52) U.S. Cl. ............... 514/254.01; 514/282; 514/327; 514/649
(58) Field of Search ................... 514/254.01, 282, 514/327, 649

(56) References Cited

U.S. PATENT DOCUMENTS

| 4,018,830 A | * | 4/1977 | Christy ............... 260/570.9 |
| 4,161,529 A | * | 7/1979 | Beregi et al. ............ 424/274 |
| 5,034,419 A | * | 7/1991 | Aubard et al. ............ 514/649 |
| 5,190,965 A | * | 3/1993 | Ruigt et al. ............ 514/401 |
| 5,731,307 A | * | 3/1998 | Desai .................. 514/217 |

* cited by examiner

*Primary Examiner*—Raymond Henley, III
(74) *Attorney, Agent, or Firm*—Peter C. Richardson; Paul H. Ginsburg; Jolene W. Appleman

(57) ABSTRACT

The present invention relates to a method of treating depression, especially refractory depression, in a mammal, including a human, by administering to the mammal a sigma receptor ligand in combination with an antidepressant agent. It also relates to pharmaceutical compositions containing a pharmaceutically acceptable carrier, a sigma receptor ligand and a serotonin reuptake inhibitor.

30 Claims, No Drawings

COMBINATION TREATMENT FOR DEPRESSION

CROSS REFERENCE TO RELATED APPLICATIONS

This application claims priority under 35 U.S.C. 119(e) of priority application Ser. No. 60/263,278 filed Jan. 22, 2001.

BACKGROUND OF THE INVENTION

The present invention relates to a method of treating depression, especially refractory depression, in a mammal, including a human, by administering to the mammal a sigma receptor ligand in combination with a Serotonin Reuptake Inhibitor (SRI). It also relates to pharmaceutical compositions containing a pharmaceutically acceptable carrier, a sigma receptor ligand and a Serotonin Reuptake Inhibitor (SRI).

Major depression is characterized by feelings of intense sadness and despair, mental slowing and loss of concentration, pessimistic worry, agitation, and self-deprecation. Physical changes also occur, especially in severe or "melancholic" depression. These include insomnia or hypersomnia, anorexia and weight loss (or sometimes overeating), decreased energy and libido, and disruption of normal circadian rhythms of activity, body temperature, and many endocrine functions.

Serotonin Selective Reuptake Inhibitors (SSRIs) currently provide efficacy in the treatment of major depressive disorder (MDD) and are generally perceived by psychiatrists and primary care physicians as effective, well-tolerated and easily administered. However, they are associated with undesirable features, such as high incidence of sexual dysfunction, delayed onset of action and a level of non-responsiveness estimated to be as high as 30% (see M. J. Gitlin, *Journal of Clinical Psychiatry*, 1994, 55, 406–413 and R. T. Segraves, *Journal of Clinical Psychiatry*, 1992, 10(2), 4–10). Preclinical and clinical evidence has indicated that the sexual dysfunction associated with SSRI therapy can be reduced through the use of monoamine reuptake inhibitors (SRI) and dopamine reuptake inhibitors (DRIs), such as bupropion (see A. K. Ashton, *Journal of Clinical Psychiatry*, 1998, 59(3), 112–115). Furthermore, the combination of SRI and DRI may hasten the onset of action as well as offering relief to refractory patients, possibly through a synergistic mechanism (see R. D. Marshall et al, *Journal of Psychopharmacology*, 1995, 9(3), 284–286) and prove beneficial in the treatment of substance abuse and attention deficit hyperactivity disorder (ADHD) according to Barrickman et al, *Journal of the American Academy of Child and Adolescent Psychology*, 1995, 34(5), 649 and Shekim et al, *Journal of Nervous and Mental Disease*, 1989, 177(5), 296.

SUMMARY OF THE INVENTION

The present invention relates to a pharmaceutical composition for the treatment of depression, especially refractory depression, comprising: (a) a compound that exhibits activity as a serotonin reuptake inhibitor, or a pharmaceutically acceptable salt thereof; (b) a sigma receptor ligand or pharmaceutically acceptable salt thereof; and (c) a pharmaceutically acceptable carrier; wherein the active agents "a" and "b" above are present in amounts that render the composition effective in treating, respectively, anxiety or depression, especially refractory depression.

This invention also relates to a method of treating depression in a mammal, comprising administering to said mammal, respectively, an antidepressant effective amount of a pharmaceutical composition comprising: (a) a serotonin reuptake inhibitor (SRI) compound that exhibits activity as an antidepressant, or a pharmaceutically acceptable salt thereof; (b) a sigma receptor ligand or pharmaceutically acceptable salt thereof; and (c) a pharmaceutically acceptable carrier; wherein the active agents "a" and "b" above are present in amounts that render the composition effective in treating, respectively, anxiety or depression, especially refractory depression.

This invention also relates to a method of treating depression in a mammal, comprising administering to said mammal: (a) a serotonin reuptake inhibitor (SRI) compound that exhibits activity as an antidepressant, or a pharmaceutically acceptable salt thereof; and (b) a sigma receptor ligand or pharmaceutically acceptable salt thereof; wherein the active agents "a" and "b" above are present in amounts that render the combination of the two agents effective in treating, respectively, anxiety or depression, especially refractory depression.

It will be appreciated that when using a combination method of the present invention, referred to immediately above, both the sigma receptor ligand and the SRI antidepressant agent will be administered to a patient within a reasonable period of time. The compounds may be in the same pharmaceutically acceptable carrier and therefore administered simultaneously. They may be in separate pharmaceutical carriers such as conventional oral dosage forms that are taken simultaneously. The term combination, as used above, also refers to the case where the compounds are provided in separate dosage forms and are administered sequentially. Therefore, by way of example, the SRI antidepressant agent may be administered as a tablet and then, within a reasonable period of time, the sigma receptor ligand may be administered either as an oral dosage form such as a tablet or a fast-dissolving oral dosage form. By a "fast dissolving oral formulation" is meant, an oral delivery form which when placed on the tongue of a patient, dissolves within about seconds.

The compositions of the present invention that contain a sigma receptor ligand and an SRI antidepressant are useful for the treatment of depression, especially refractory depression. As used herein, the term "depression" includes depressive disorders, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias, seasonal affective disorder, or bipolar disorders or manic depression, for example, bipolar I disorder, bipolar II disorder and cyclothymic disorder.

Other mood disorders encompassed within the term "depression" include dysthymic disorder with early or late onset and with or without atypical features; dementia of the Alzheimer's type, with early or late onset, with depressed mood; vascular dementia with depressed mood, disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood.

The compositions of the present invention are especially useful for the treatment of refractory depression where the use of an antidepressant is generally prescribed. By the use of a combination of a sigma receptor ligand and an SRI antidepressant agent in accordance with the present invention, it is possible to treat refractory depression in patients for whom conventional antidepressant therapy might not be wholly successful.

Examples of Serotonin Reuptake Inhibitors (SRI) that may be used in the methods and pharmaceutical compositions of this invention are compounds of the formula

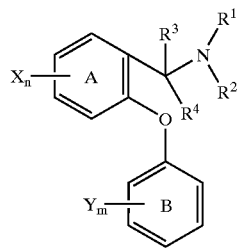

I wherein phenyl ring A and phenyl ring B can each, independently, be replaced by a naphthyl group, and wherein when phenyl ring A is replaced by a naphthyl group, the ethereal oxygen of structure I and the carbon to which $R^3$, $R^4$ and $NR^1R^2$ are attached, are attached to adjacent ring carbon atoms of the naphthyl group and neither of said adjacent ring carbon atoms is also adjacent to a fused ring carbon atom of said naphthyl group;

n and m are, selected, independently, from one, two and three;

$R^1$ and $R^2$ are selected, independently, from hydrogen ($C_1$–$C_4$)alkyl, ($C_2$–$C_4$)alkenyl, and ($C_2$–$C_4$)alkynyl, or $R^1$ and $R^2$, together with the nitrogen to which they are attached, form a four to eight membered saturated ring containing one or two heteroatoms, including the nitrogen to which $R^1$ and $R^2$ are attached, wherein the second heteroatom, when present, is selected from oxygen, nitrogen and sulfur, and wherein said ring may optionally be substituted at available binding sites with from one to three substituents selected, independently, from hydroxy and ($C_1$–$C_6$)alkyl;

$R^3$ and $R^4$ are selected, independently, from hydrogen and ($C_1$–$C_4$)alkyl optionally substituted with from one to three fluorine atoms, or $R^3$ and $R^4$ together with the carbon to which they are attached, form a four to eight membered saturated carbocyclic ring, and wherein said ring may optionally be substituted at available binding sites with from one to three substituents selected, independently, from hydroxy and ($C_1$–$C_6$)alkyl;

or $R^2$ and $R^3$, together with the nitrogen to which $R^2$ is attached and the carbon to which $R^3$ is attached, form a four to eight membered saturated ring containing one or two heteroatoms, including the nitrogen to which $R^2$ is attached, wherein the second heteroatom, when present, is selected from oxygen, nitrogen and sulfur, and wherein said ring may optionally be substituted at available binding sites with from one to three substituents selected, independently, from hydroxy and ($C_1$–$C_6$)alkyl;

each X and each Y is selected, independently, from hydrogen, halo (i.e., chloro, fluoro, bromo or iodo), ($C_1$–$C_4$) alkyl optionally substituted with from one to three fluorine atoms, ($C_1$–$C_4$)alkoxy optionally substituted with from one to three fluorine atoms, cyano, nitro, amino, ($C_1$–$C_4$) alkylamino, di-[($C_1$–$C_4$)alkyl]amino, $NR^5(C=O)(C_1$–$C_4)$ alkyl wherein $R^5$ is hydrogen or ($C_1$–$C_6$)alkyl, and $SO_p$ ($C_1$–$C_6$)alkyl wherein p is zero, one or two; and with the proviso that: (a) no more than one of $NR^1R^2$, $CR^3R^4$ and $R^2NCR^3$ can form a ring; and (b) at least one X must be other than hydrogen when (i) $R^3$ and $R^4$ are both hydrogen, (ii) $R^1$ and $R^2$ are selected, independently, from hydrogen and ($C_1$–$C_4$)alkyl, and (iii) ring B is mono- or disubstituted with, respectively, one or two halo groups; and the pharmaceutically acceptable salts thereof.

Pharmaceutically acceptable acid addition salts of the compounds of formula I can also be used in the methods and pharmaceutical composition of this invention. Examples of pharmaceutically acceptable acid addition salts of the compounds of formula I are the salts of hydrochloric acid, p-toluenesulfonic acid, fumaric acid, citric acid, succinic acid, salicylic acid, oxalic acid, hydrobromic acid, phosphoric acid, methanesulfonic acid, tartaric acid, maleic acid, di-p-toluoyl tartaric acid, acetic acid, sulfuric acid, hydroiodic acid and mandelic acid.

Unless otherwise indicated, the term "halo", as used herein, includes fluoro, chloro, bromo and iodo.

Unless otherwise indicated, the term "alkyl", as used herein, may be straight, branched or cyclic, and may include straight and cyclic moieties as well as branched and cyclic moieties.

The term "treatment", as used herein, refers to reversing, alleviating, inhibiting the progress of, or preventing the disorder or condition to which such term applies, or one or more symptoms of such condition or disorder. The term "treatment", as used herein, refers to the act of treating, as "treating" is defined immediately above.

The compounds of formula I may have optical centers and therefore may occur in different enantiomeric configurations. All enantiomers, diastereomers, and other stereoisomers of such compounds of formula I, as well as racemic and other mixtures thereof are included in the pharmaceutical compositions and methods of this invention.

The pharmaceutical compositions and methods of this invention also relates to all radiolabelled forms of the compounds of the formula I. Preferred radiolabelled compounds of formula I are those wherein the radiolabels are selected from as $^3H$, $^{11}C$, $^{14}C$, $^{18}F$, $^{123}I$ and $^{125}I$. Such radiolabelled compounds are useful as research and diagnostic tools in metabolism pharmacokinetics studies and in binding assays in both animals and man.

"Chemical dependency," as used herein, means an abnormal craving or desire for, or an addiction to a drug. Such drugs are generally administered to the affected individual by any of a variety of means of administration, including oral, parenteral, nasal or by inhalation. Examples of chemical dependencies treatable by the methods of the present invention are dependencies on alcohol, nicotine, cocaine, heroin, Phenobarbital, and benzodiazepines (e.g., Valium (trademark)). "Treating a chemical dependency," as used herein, means reducing or alleviating such dependency.

Preferred embodiments of formula I include the following compounds of the formula I and their pharmaceutically acceptable salts:

[2-(3,4-Dichlorophenoxy)-5-fluorobenzyl]-dimethylamine;

[2-(3,4-Dichlorophenoxy)-5-fluorobenzyl]-methylamine;

[2-(3,4-Dichlorophenoxy)-5-trifluoromethylbenzyl]-dimethylamine;

N-[4-(3,4-Dichlorophenoxy)-3-dimethylaminomethylphenyl]-acetamide;

1-[2-(3,4-Dichlorophenoxy)phenyl]-ethyl}-dimethylamine;

[2-(3,4-Dichlorophenoxy)-4-trifluoromethylbenzyl]-dimethylamine;

[2-(3,4-Dichlorophenoxy)-4-trifluoromethylbenzyl]-methylamine;
[4-Chloro-2-(3,4-dichlorophenoxy)-benzyl]-methylamine;
{1-[2-(3,4-Dichlorophenoxy)-5-fluorophenyl]-ethyl}-methylamine;
{1-[2-(3,4-Dichlorophenoxy)phenyl}-ethyl}-methylamine;
{1-[2-(4-Chlorophenoxy)phenyl]ethyl}-methylamine;
[2-(3,4-Dichlorophenoxy)-5-methoxybenzyl]-methylamine;
[2-(4-Chlorophenoxy)-5-fluorobenzyl]-methylamine; and
{1-[2-(4-Chlorophenoxy)-5-fluorophenyl]-ethyl}-methylamine.
[2-(3,4-Dichlorophenoxy)-5-methylbenzyl]-dimethylamine;
[4-Bromo-2-(3,4-dichlorophenoxy)-benzyl]-methylamine;
[5-Bromo-2-(3,4-dichlorophenoxy)-benzyl]-methylamine;
[2-(3,4-Dichlorophenoxy)-4,5-dimethoxybenzyl]-methylamine;
[2-(3,4-Dichlorophenoxy)-4-methoxybenzyl]-dimethylamine;
4-(3,4-Dichlorophenoxy)-3-methylaminomethyl-benzonitrile;
[2-(3,4-Dichlorophenoxy)-4,5-dimethylbenzyl]-methylamine;
3-(3,4-Dichlorphenoxy)-4-methylaminomethyl-benzonitrile;
(+)-{1-[2-(3,4-Dichlorophenoxy)-5-fluorophenyl]-ethyl}-methylamine;
(−)-{1-[2-(3,4-Dichlorophenoxy)-5-fluorophenyl]-ethyl}-methylamine;
[2-(3,4-Dichlorophenoxy)-5-trifluoromethyl-benzyl]-methylamine;
[2-(3,4-Dichlorophenoxy)-4-methoxybenzyl]-methylamine;
[2-(4-Chloro-3-fluorophenoxy)-5-fluorobenzyl]-methylamine;
[2-(3-Chloro-4-fluorophenoxy)-5-fluorobenzyl]-methylamine;
(+/−)-2-[2-(3,4-Dichlorophenoxy)-5-fluorophenyl]-pyrrolidine;
(−)-2-[2-(3,4-Dichlorophenoxy)-5-fluorophenyl]-pyrrolidine;
(+)-2-[2-(3,4-Dichlorophenoxy)-5-fluorophenyl]-pyrrolidine; and
2-[2-(3,4-Dichlorophenoxy)-5-fluorophenyl]-N-methylpyrrolidine.

Other embodiments of formula I include the following compounds and their pharmaceutically acceptable salts:
{1-[2-(3,4-Dichlorophenoxy)-5-fluorophenyl]-1-methylethyl}-methylamine;
{1-[2-(3,4-Dichlorophenoxy)-5-fluorophenyl]-1-methylethyl}-dimethylamine;
[4-Chloro-2-(4-chlorophenoxy)-5-fluorobenzyl]-methylamine;
[2-(3,4-Dichlorophenoxy)-5-fluoro-4-methoxybenzyl]-methylamine;
[4-(3,4-Dichlorophenoxy)-3-(dimethylaminomethyl)-phenyl]-dimethylamine

[5-Fluoro-2-(4-fluoro-3-methoxyphenoxy)-benzyl]-dimethylamine;
[2-(4-Chlorophenoxy)-5-isopropylbenzyl]-methylamine;
{1-[2-(4-Chlorophenoxy)-5-trifluoromethylphenyl]-ethyl}-methylamine;
[2-(4-Chlorophenoxy)-4,5-dimethylbenzyl]-methylamine;
{1-[5-Chloro-2(3,4-dichlorophenoxy)phenyl]-propyl}-methylamine;
[2-(3,4-Dichlorophenoxy)-5-methylsulfanyl-benzyl]-methylamine;
{1-[2-(3,4-Dichlorophenoxy)-5-methylsulfanyl-phenyl]-ethyl}-methylamine;
{1-[2-(3,4-Dichlorophenoxy)-5-methylsulfanyl-phenyl]-1-methylethyl}-methylamine;
[2-(3,4-Dichlorophenoxy)-5-methylsulfanyl-benzyl]-dimethylamine;
[2-(3,4-Dichlorophenoxy)-5-methanesulfinyl-benzyl]-dimethylamine;
[2-(3,4-Dichlorophenoxy)-5-methanesulfinyl-benzyl]-methylamine;
[2-(3,4-Dichlorophenoxy)-5-methanesulfonyl-benzyl]-methylamine;
[2-(3,4-Dichlorophenoxy)-5-methanesulfonyl-benzyl]-dimethylamine;
[2-(3,4-Dichlorophenoxy)-5-(propane-2-sulfonyl)-benzyl]-methylamine;
2-[2-(3,4-Dichlorophenoxy)-5-fluorophenyl]-piperidine;
2-[2-(3,4-Dichlorophenoxy)-5-fluorophenyl]-1-methyl-piperidine;
3-[2-(3,4-Dichlorphenoxy)-5-fluorophenyl]-4-methyl-morpholine;
2-[2-(3,4-Dichlorophenoxy)-5-fluorophenyl]-1,2-dimethyl-piperidine;
{1-[2-(3,4-Dichlorophenoxy)-5-fluorophenyl]-cyclopropyl}-dimethylamine;
2-[2-(3,4-Dichlorophenoxy)-5-fluorophenyl]-1,5-dimethyl-pyrrolidine;
3-[2-(3,4-Dichlorophenoxy)-5-fluorophenyl]-4-methyl-thiomorpholine;
{1-[2-(3,4-Dichlorophenoxy)-5-fluorophenyl]-cyclopentyl}-methylamine;
{1-[2-(3,4-Dichlorophenoxy)-5-(propane-2-sulfonyl)-phenyl]-ethyl-methylamine; and
[4-Chloro-2-(3,4-dichlorophenoxy)-5-methenesulfonyl-benzyl]-methylamine.

Other embodiments of this invention relate to the compound of the formula I wherein m is zero, n is one, $R^3$ and $R^4$ are hydrogen, X is chloro, bromo, iodo or methyl, $R^1$ is hydrogen and $R^2$ is methyl.

Other examples of Serotonin Reuptake Inhibitors (SRI) that can be used in the method and pharmaceutical compositions of this invention are compounds of the formula

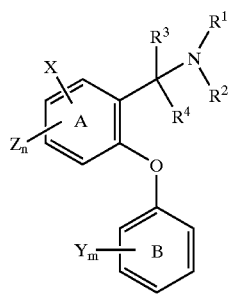

wherein phenyl ring A and phenyl ring B can each, independently, be replaced by a naphthyl group, and wherein when phenyl ring A is replaced by a naphthyl group, the ethereal oxygen of Formula II and the carbon to which $R^3$, $R^4$ and $NR^1R^2$ are attached, are attached to adjacent ring carbon atoms of the naphthyl group and neither of said adjacent ring carbon atoms is also adjacent to a fused ring carbon atom of said naphthyl group;

n and m are selected, independently, from one, two and three;

$R^1$ and $R^2$ are selected, independently, from hydrogen, $(C_1-C_4)$alkyl, $(C_2-C_4)$alkenyl, and $(C_2-C_4)$alkynyl, or $R^1$ and $R^2$, together with the nitrogen to which they are attached, form a four to eight membered saturated ring containing one or two heteroatoms, including the nitrogen to which $R^1$ and $R^2$ are attached, wherein the second heteroatom, when present, is selected from oxygen, nitrogen and sulfur, and wherein said ring may optionally be substituted at available binding sites with from one to three substituents selected, independently, from hydroxy and $(C_1-C_6)$alkyl;

$R^3$ and $R^4$ are selected, independently, from hydrogen and $(C_1-C_4)$alkyl optionally substituted with from one to three fluorine atoms, or $R^3$ and $R^4$ together with the carbon to which they are attached form a four to eight membered saturated carbocyclic ring, and wherein said ring may optionally be substituted at available binding sites with from one to three substituents selected, independently, from hydroxy and $(C_1-C_6)$alkyl;

or $R^2$ and $R^3$, together with the nitrogen to which $R^2$ is attached and the carbon to which $R^3$ is attached, form a four to eight membered saturated ring containing one or two heteroatoms, including the nitrogen to which $R^2$ is attached, wherein the second heteroatom, when present, is selected from oxygen, nitrogen and sulfur, and wherein said ring may optionally be substituted at available binding sites with from one to three substituents selected, independently, from hydroxy and $(C_1-C_6)$alkyl;

each X is selected, independently, from phenyl, heteroaryl (e.g., furan, thiophene, pyrrole, thiazole, isothiazole, oxazole, isoxazole, imidazole, 1,2,4-oxadiazole, 1,2,4-thiadiazole, 1,2,4-triazole, 1,2,3,-triazole, tetrazole, pyridine, pyrimidine, pyrazine, quinoline, isoquinoline, quinazoline, quinoxaline, benzothiophene, benzofuran, benzimidazole, benzisoxazole, benzisothiazole and indole) or heterocycle (e.g., imidazolidine, oxazolidine, thiazolidine, pyrrolidine, piperidine, morpholine) groups as defined below and may be further substituted by hydrogen, halo (i.e., fluorine, chlorine, bromine, iodine), $(C_1-C_4)$alkyl optionally substituted with from one to three fluorine atoms, $(C_1-C_4)$alkoxy optionally substituted with from one to three fluorine atoms, cyano, nitro, amino, hydroxy, carbonyl, $(C_1-C_4)$alkylamino, di-[$(C_1-C_4)$alkyl]amino, $NR^5(C=O)(C_1-C_4)$alkyl, $SO_2NR^5R^6$ and $SO_p(C_1-C_6)$alkyl, wherein $R^5$ and $R^6$ are selected, independently, from hydrogen and $(C_1-C_6)$alkyl, and p is zero, one or two;

each Y is selected, independently, from hydrogen, halo (i.e., chloro, fluoro, bromo or iodo), $(C_1-C_4)$alkyl optionally substituted with from one to three fluorine atoms, $(C_1-C_4)$alkoxy optionally substituted with from one to three fluorine atoms, cyano, nitro, amino, $(C_1-C_4)$alkylamino, di-[$(C_1-C_4)$alkyl]amino, $NR^5(C=O)(C_1-C_4)$alkyl, $SO_2NR^5R^6$ and $SO_p(C_1-C_6)$alkyl, wherein $R^5$ and $R^6$ are selected, independently, from hydrogen and $(C_1-C_6)$alkyl, and p is zero, one or two; and each Z is selected independently from hydrogen, halo (i.e., chloro, fluoro, bromo or iodo), $(C_1-C_4)$alkyl optionally substituted with from one to three fluorine atoms, $(C_1-C_4)$alkoxy;

and the pharmaceutically acceptable salts thereof. Compounds of formula II, and their pharmaceutically acceptable salts, have activity in inhibiting reuptake of serotonin, dopamine, and norepinephrine.

In one embodiment, ring B is phenyl, not replaced with a naphthyl group. In another embodiment, phenyl ring B in the compounds of formula II is replaced with a naphthyl group.

In a preferred embodiment when ring B is phenyl, each Y is hydrogen or halo. In a more preferred embodiment, m is 1 or 2, and each Y is chlorine.

In another embodiment, compounds of formula II, or pharmaceutically acceptable salts, thereof are described above, but wherein X is selected from furan, thiophene, pyrrole, and 1,2,3-triazole, and wherein X may be further substituted.

In another embodiment, compounds of formula II or salts thereof are described above, but wherein each Z is selected from hydrogen and halo. Preferably, Z is hydrogen.

In a further embodiment, compounds of formula II or salts thereof are described above, wherein $R^3$ and $R^4$ are independently selected from hydrogen and unsubstituted $(C_1-C_4)$alkyl. Preferably, one or both of $R^3$ and $R^4$ are hydrogen.

In a further embodiment, formula II or salts thereof, wherein $R^1$ and $R^2$ are independently selected from hydrogen and unsubstituted $(C_1-C_4)$alkyl. Preferably, one of $R^1$ and $R^2$ is hydrogen and the other of $R^1$ and $R^2$ is $(C_1-C_4)$ alkyl. More preferably, one of $R^1$ and $R^2$ is hydrogen and the other of $R^1$ and $R^2$ is methyl.

The methods and pharmaceutical compositions of this invention also relates to the pharmaceutically acceptable acid addition salts of the compounds of formula II. Examples of pharmaceutically acceptable acid addition salts of the compounds of formula II are the salts of hydrochloric acid, p-toluenesulfonic acid, fumaric acid, citric acid, succinic acid, salicylic acid, oxalic acid, hydrobromic acid, phosphoric acid, methanesulfonic acid, tartaric acid, maleic acid, di-p-toluoyl tartaric acid, acetic acid, sulfuric acid, hydroiodic acid and mandelic acid.

Unless otherwise indicated, the term "halo", as used herein, includes fluoro, chloro, bromo and iodo.

Unless otherwise indicated, the term "alkyl", as used herein, may be straight, branched or cyclic, and may include straight and cyclic moieties as well as branched and cyclic moieties.

When reference is made to $SO_p(C_1-C_6)$alkyl, and p is two, this indicates a sulfone, in other words, $S(=O)_2(C_1-C_6)$alkyl.

The term "treatment", as used herein, refers to reversing, alleviating, inhibiting the progress of, or preventing the disorder or condition to which such term applies, or one or more symptoms of such condition or disorder. The term "treatment", as used herein, refers to the act of treating, as "treating" is defined immediately above.

When reference is made herein to a disorder or condition that can be treated by inhibiting the reuptake of serotonin, dopamine, or norepinephrine, this means that the disorder or condition has as a contributing factor at least one of serotonin, dopamine, or norepinephrine-mediated neurotransmission. The disorder or condition may have as a contributing factor one, two, or all three of the aforementioned types of neurotransmission. Moreover, a factor or factors other than serotonin, dopamine, or norepinephrine-mediated neurotransmission may also contribute to the disorder or condition. Disorders and conditions to which serotonin, dopamine, or norepinephrine-mediated neurotransmission contribute can be ascertained by those of ordinary skill in the art and include, but are not limited to, for example, addiction and substance abuse, depression, and phobia.

The compounds of formula II may have optical centers and therefore may occur in different enantiomeric configurations. The invention includes all enantiomers, diastereomers, and other stereoisomers of such compounds of formula II, as well as racemic and other mixtures thereof.

Formula II compounds also include isotopically-labeled compounds, which are identical to those recited in formula II, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3$H, $^{11}$C, $^{14}$C, $^{18}$F, $^{123}$I and $^{125}$I. Compounds of the present invention and pharmaceutically acceptable salts of said compounds that contain the aforementioned isotopes and/or other isotopes of other atoms are within the scope of this invention. Isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances.

"Chemical dependency," as used herein, means an abnormal craving or desire for, or an addiction to a drug. Such drugs are generally administered to the affected individual by any of a variety of means of administration, including oral, parenteral, nasal or by inhalation. Examples of chemical dependencies treatable by the methods of the present invention are dependencies on alcohol, nicotine, cocaine, heroin, Phenobarbital, and benzodiazepines (e.g., Valium (trademark)). "Treating a chemical dependency," as used herein, means reducing or alleviating such dependency.

Preferred embodiments of the compounds of formula II include the following compounds of the formula II and their pharmaceutically acceptable salts:

[4-(3,4-Dichlorophenoxy)-biphenyl-3-ylmethyl]-methylamine;

[2-(3,4-Dichlorophenoxy)-5-thiophen-3-ylbenzyl]-methylamine;

[2-(3,4-Dichlorophenoxy)-4-thiophen-3-ylbenzyl]-methylamine;

[2-(3,4-Dichlorophenoxy)-4-furan-2-ylbenzyl]-methylamine;

[2-(3,4-Dichlorophenoxy)-5-furan-2-ylbenzyl]-methylamine;

N-[4'-(3,4-Dichlorphenoxy)-3'-methylaminomethyl-biphenyl-3-yl]-acetamide;

[2-(3,4-Dichlorophenoxy)-5-thiophen-2-ylbenzyl]-methylamine;

[4-(3,4-Dichlorophenoxy)-4'-fluoro-biphenyl-3-ylmethyl]-methylamine;

[2-(3,4-Dichlorophenoxy)-5-[1,2,3]triazol-1-ylbenzyl]-methylamine;

[2-(3,4-Dichlorophenoxy)-5-[1,2,3]triazol-2-ylbenzyl]-methylamine;

[2-(3,4-Dichlorophenoxy)-5-pyridin-2-ylbenzyl]-methylamine;

[2-(3,4-Dichlorophenoxy)-5-pyridin-3-ylbenzyl]-methylamine;

1-[4-(3,4-Dichlorophenoxy)-3-methylaminomethylphenyl]-1H-pyrazol-3-ylamine;

[2-(3,4-Dichlorophenoxy)-5-pyridin-4-ylbenzyl]-methylamine;

[3-(3,4-Dichlorophenoxy)-biphenyl4-ylmethyl]-methylamine;

[4-(3,4-Dichlorophenoxy)-4'-methyl-biphenyl-3-ylmethyl]-methylamine;

[2-(3,4-Dichlorophenoxy)-4-thiophen-2-ylbenzyl]-methylamine;

[2-(3,4-Dichlorophenoxy)-5-pyrimidin-2-ylbenzyl]-methylamine;

[2-(3,4-Dichlorophenoxy)-5-pyrimidin-4-ylbenzyl]-methylamine;

[2-(3,4-Dichlorophenoxy)-5-(2-methylpyrimidin-4-yl)-benzyl]-methylamine;

{1-[2-(3,4-Dichlorophenoxy)-5-(2-methylpyrimidin-4-yl)-phenyl]-ethyl}-methylamine;

4-[4-(3,4-Dichlorophenoxy)-3-(5-methylpyrimidin-2-yl)-phenyl]-2-methylpyrimidine;

[2-(4-Chlorophenoxy)-5-(1-methyl-1H-pyrrol-3-yl)-benzyl]-dimethylamine;

[5-(1-methyl-1H-pyrrol-3-yl)-2-(naphthalen-2-yloxy)-benzyl]-dimethyl amine;

[5-imidazol-1-yl-2-(naphthalen-2-yloxy)-benzyl]-dimethylamine;

1,5,5-Trimethyl-3-[3-methylaminomethyl-4-(naphthalen-2-yloxy)-phenyl]-imidazolidine-2,4-dione;

1-Methyl-3-[3-methylaminomethyl-4-(naphthalen-2-yloxy)-phenyl]-imidazolidine-2,4-dione, 3-[3-Methylaminomethyl-4-(naphthalen-2-yloxy)-phenyl]-thiazolidine-2,4-dione;

3-[3-Methylaminomethyl-4-(naphthalen-2-yloxy)-phenyl]-oxazolidine-2,4-dione;

3-[3-Methylaminomethyl-4-(naphthalen-2-yloxy)-phenyl]-oxazolidin-2-one;

3-[3-Methylaminomethyl-4-(naphthalen-2-yloxy)-phenyl]-thiazolidin-2-one;

1-Methyl-3-[3-methylaminomethyl-4-(naphthalen-2-yloxy)-phenyl]-imidazolidin-2-one;

1-Methyl-3-[3-methylaminomethyl-4-(naphthalen-2-yloxy)-phenyl]-tetrahydro-pyrimidin-2-one;

1-[4-(3,4-Dichlorophenoxy)-3-methylaminomethyl-phenyl]-3-methyl-tetrahydropyrimidin-2-one;

1-[4-(3,4-Dichlorophenoxy)-3-methylaminomethyl-phenyl]-3-methylimidazolidin-2-one;

3-[4-(3,4-Dichlorophenoxy)-3-methylaminomethyl-phenyl]-thiazolidin-2-one;

3-[4-(3,4-Dichlorophenoxy)-3-methylaminomethyl-phenyl]-oxazolidin-2-one;

[2-(3,4-Dichlorophenoxy)-5-(2-methylthiazol-4-yl)-benzyl]-methylamine;

[2-(3,4-Dichlorophenoxy)-5-(2-methyloxazol-4-yl)-benzyl]-methylamine;

[2-(3,4-Dichlorophenoxy)-5-(2,5-dimethyloxazol-4-yl)-benzyl]-methylamine;

[2-(3,4-Dichlorophenoxy)-5-(2,5-dimethylthiazol-4-yl)-benzyl]-methylamine;

[2-(3,4-Dichlorophenoxy)-5-(5-methyl-[1,2,4]thiadiazol-3-yl)-benzyl]-methylamine;

[2-(3,4-Dichlorophenoxy)-5-(5-methyl-[1,2,4oxadiazol-3-yl)-benzyl]-methylamine;

[2-(3,4-Dichlorophenoxy)-5-[1,2,3]oxadiazol-4-yl-benzyl]-methylamine;

[2-(3,4-Dichlorophenoxy)-5-(5-methyl-[1,2,3]thiadiazol-4-yl)-benzyl]-methylamine;

[2-(3,4-Dichlorophenoxy)-5-(2,4-dimethyloxazol-5-yl)-benzyl]-methylamine;

[2-(3,4-Dichlorophenoxy)-5-(2,4-dimethyloxiazol-5-yl)-benzyl]-methylamine;

[2-(3,4-Dichlorophenoxy)-5-[1,2,4]triazol-1-ylbenzyl]-methylamine;

[2-(3,4-Dichlorophenoxy)-5-(3-methyl-[1,2,4]triazol-1-yl)-benzyl]-methylamine;

[2-(4-Chlorophenoxy)-5-(3,5-dimethyl-[1,2,4]triazol-1-yl)-benzyl]-methylamine;

[2-(4-Chlorophenoxy)-5-tetrazol-1-ylbenzyl]-methylamine;

[2-(4-Chlorophenoxy)-5-(5-methyltetrazol-1-yl)-benzyl]-di methylamine;

[2-(4-Chlorophenoxy)-5-[1,2,4]triazol-4-ylbenzyl]-dimethylamine;

[2-(4-Chlorophenoxy)-5-(1-methyl-1H-tetrazol-5-yl)-benzyl]-dimethylamine; and

{1-[2-(3,4-Dichlorophenoxy)-5-(1-methyl-I H-tetrazol-5-yl)-phenyl]-ethyl}-dimethylamine.

Suitable classes of sigma receptor ligands that may be used in the compositions and methods of this invention include the following compounds and their pharmaceutically acceptable salts:

igmesine [N-(1,4-diphenyl-1-ethyl-3-buten-1-yl)-N-methyl-cyclopropanemethanamine hydrochloride];

siramesine [1'-(4-(1-(4-fluorophenyl)-1H-indol-3-yl)-1-butyl)-spiro(isobenzofuran-1(3H), 4'-piperidine];

E-5842 [4-(4-fluorophenyl)-1,2,3,6-tetrahydro-1-(4-(2H-1,2,4-triazol-1-yl)butylpyridine];

MS-377 [(R)-1-(4-chlorophenyl)-3-[4-(2-methoxyethyl)-piperazin-1-yl]methyl-2-pyrrolidinone];

NE-100 [N,N-dipropyl-2-[4-methoxy-3-(2-phenylethoxy)phenyl]ethylamine];

OPC-14523 [1-(3-(4-(3-chlorophenyl)-1-piperazinyl)propyl)-5-methoxy-3,4-dihydro-2-quinolinone];

SA-4503 [1-(3,4-dimethoxyphenethyl)-4-(3-phenylpropyl)-piperazine];

SR-31742A [(Z)-1-(3-(3-chloro-4-cyclohexylphenyl)-2-propenyl)-hexahydro-1H-azepine];

haloperidol [4-[4-(4-chlorophenyl)-4-hydroxy-1-piperidinyl]-1-(4-fluorophenyl)-1-butanone];

cis-7-(cyclopentanespiro-3'-glutaramidomethyl)-2-(2-phenethyl)-perhydro-1H-pyrido[1,2a]pyrazine;

SKF-10,047 [2S-(2α, 6α),11R]-1,2,3,4,5,6-hexahydro-6,11-dimethyl-3-(2-propenyl)-2,6-methano-3-benzazocin-8-ol];

Dextromethorphan [(+)-3-methoxy-17-methyl-9α,13α,14α-morphinan]; and

BMY-14802 [α-(4-fluorophenyl)-4-(5-fluoro-2-pyrimidinyl)-1-piperazinebutanol monohydrochloride].

DETAILED DESCRIPTION OF THE INVENTION

The following references refer to novel biaryl ether derivatives useful as monoamine reuptake inhibitors that exhibit activity as a serotonin reuptake inhibitor and that can be used, in combination with sigma receptor ligands in the pharmaceutical compositions and methods of this invention, and to methods of preparing the same: PCT application No.: PCT/IB00/01373 Filed Sep. 27, 2000 and PCT application No. PCT/IB00/00108 filed Feb 2, 2000.

U.S. Pat. No. 4,018,830, issued Apr. 19, 1997, refers to phenylthioaralkylamines and 2-phenylthiobenzylamines which are active as antiarrhythmics.

WO 97/17325, International Publication Date May 15, 1997, refers to derivatives of N,N-dimethyl-2-(arylthio) benzylamine which selectively influence serotonin transport in the central nervous system and are useful as antidepressants.

U.S. Pat. No. 5,190,965, issued Mar. 2, 1993, and U.S. Pat. No. 5,430,063, issued Jul. 4, 1995, refer to phenoxyphenyl derivatives which have utility in the treatment of depression.

U.S. Pat. No. 4,161,529, issued Jul. 17, 1979, refers to pyrrolidine derivatives that possess anticholesteremic and hypolipemic activity.

U.S. Provisional Application No. 60/121313, filed Feb. 23, 1999, refers to biaryl ethers that have activity in inhibiting reuptake of both serotonin and dopamine.

The SRI antidepressants of the formula I can be prepared as described in the following patent application, which is referred to above and incorporated herein by reference in its entirety; PCT application NO. PCT/IB00/01373 filed Sep. 27, 2000. SRI antidepressants of Formula II can be prepared as described in the following patent application, which is referred to above and incorporated herein by reference in its entirety: PCT application No. PCT/IB00/00108 filed Feb. 2, 2000. All the foregoing patents and patent applications are incorporated herein by reference in their entirety.

The sigma receptor ligands that can be used, together with an SRI antidepressant agent in the pharmaceutical compositions and methods of this invention are those compounds and pharmaceutically acceptable salts described in the following references:

igmesine [N-(1,4-diphenyl-1-ethyl-3-buten-1-yl)-N-methyl-cyclopropanemethanamine hydrochloride] U.S. Pat. No. 5,034,419 issued Jul. 23, 1991;

siramesine [1'-(4-(1-(4-fluorophenyl)-1H-indol-3-yl)-1-butyl)-spiro(isobenzofuran-1(3H), 4'-piperidine] published in WO-92/22554 on Dec. 23, 1992;

E-5842 [4-(4-fluorophenyl)-1,2,3,6-tetrahydro-1-(4-(2H-1,2,4-triazol-1-yl)butylpyridine] published in WO-00/02519 on Jan. 20, 2000;

MS-377 [(R)-1-(4-chlorophenyl)-3-[4-(2-methoxyethyl)-piperazin-1-yl]methyl-2-pyrrolidinone] EP-839,805 granted May 6, 1998;

NE-100 [N,N-dipropyl-2-[4-methoxy-3-(2-phenylethoxy)phenyl]ethylamine] published in WO-93/07113 on Apr. 15, 1993;

OPC-14523 [1-(3-(4-(3-chlorophenyl)-1-piperazinyl)propyl)-5-methoxy-3,4-dihydro-2-quinolinone] EP-512,525 granted Nov. 11, 1992;

SA-4503 [1-(3,4-dimethoxyphenethyl)-4-(3-phenylpropyl)-piperazine] published in WO-95/04050 on Feb. 9, 1995;

SR-31742A [(Z)-1-(3-(3-chloro-4-cyclohexylphenyl)-2-propenyl)-hexahydro-1H-azepine] EP-461,986 granted Dec. 18, 1991;

haloperidol [4-[4-(4-chlorophenyl)-4-hydroxy-1-piperidinyl]-1-(4-fluorophenyl)-1-butanone] Belgian Patent 577,977 issued 1959;

[cis-7-(cyclopentanespiro-3'-glutaramidomethyl)-2-(2-phenethyl)-perhydro-1H-pyrido[1,2a]pyrazine] and other compounds claimed in U.S. Pat. No. 5,731,307 issued on Mar. 24, 1998;

SKF-10,047 [2S-(2α, 6α),11R]-1,2,3,4,5,6-hexahydro-6,11-dimethyl-3-(2-propenyl)-2,6-methano-3-benzazocin-8-ol published in WO 00/41684 on Jul. 20, 2000;

Dextromethorphan [(+)-3-methoxy-17-methyl-9α,13α,14α-morphinan] published in WO/0041684 on Jul. 20, 2000; and BMY-14802 [α-(4-fluorophenyl)-4-(5-fluoro-2-pyrimidinyl)-1-piperazinebutanol monohydrochloride] published in WO-00/41684 on Jul. 20, 2000.

All the foregoing patents and patent applications are incorporated herein by reference in their entirety.

This invention relates both to methods of treating depression in which the sigma receptor ligand and the SRI antidepressant agent, or pharmaceutically acceptable salts of the same, are administered together, as part of the same pharmaceutical composition, as well as to methods in which these two active agents are administered separately as part of an appropriate dose regimen designed to obtain the benefits of the combination therapy. The appropriate dose regimen, the amount of each dose administered, and specific intervals between doses of each active agent will depend upon the subject being treated and the severity of the condition. Generally, in carrying out the methods of this invention, the sigma receptor ligand will be administered to an adult human in an amount ranging from about 0.05 to about 1500 mg per day, in single or divided doses, preferably from about 5 to about 200 mg/day. The compounds may be administered on a regimen of up to 6 times per day, preferably 1 to 4 times per day, especially 2 times per day and most especially once daily. A suitable dosage level for the SRI antidepressant agent is about 0.5 to 1500 mg per day, preferably about 2.5 to 1000 mg per day, and especially about 2.5 to 500 mg per day. The compounds may be administered on a regimen of up to 6 times per day, preferably 1 to 4 times per day, especially 2 time per day and most especially once daily-variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The sigma receptor ligands, their pharmaceutically acceptable salts, and the SRI antidepressant agents and their pharmaceutically acceptable salts that are employed in the pharmaceutical compositions and methods of this invention are hereinafter also referred to as "therapeutic agents". The therapeutic agents can be administered via either the oral or parenteral route. Compositions containing both a sigma receptor ligand and an SRI antidepressant agent, or pharmaceutically acceptable salts of one or both therapeutic agents, will generally be administered orally or parenterally daily, in single or divided doses, so that the total amount of each active agent administered falls within the above guidelines.

The therapeutic agents may be administered alone or in combination with pharmaceutically acceptable carriers or diluents by either of the routes previously indicated, and such administration may be carried out in single or multiple doses. More particularly, the therapeutic agents of this invention can be administered in a wide variety of different dosage forms, i.e, they may be combined with various pharmaceutically acceptable inert carriers in the form of tablets, capsules, lozenges, troches, hard candies, suppositories, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutic agents of this invention, when administered separately (ie., not in the same pharmaceutical composition) are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic agent in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well known to those skilled in the art.

As stated above, the sigma receptor ligand and the SRI antidepressant agent may be formulated in a single pharmaceutical composition or alternatively in individual pharmaceutical compositions for simultaneous, separate or sequential use in accordance with the present invention.

Preferably the compositions according to the present invention, which contain both a sigma receptor ligands and an SRI antidepressant, as well as the pharmaceutical compositions used to deliver only one of these active agents, are in unit dosage forms such as tablets, pills, capsules, powders, granules, solutions or suspensions, or suppositories, for oral, parenteral or rectal administration, by inhalation or insufflation or administration by transdermal patches or by buccal cavity absorption wafers.

For preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing, typically, from 0.05 to about 500 mg of each of the therapeutic agents contained in the composition. The tablets or pills of the composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac acetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil, peanut oil or soybean oil, as well as elixirs and similar pharmaceutical vehicles. Suitable dispersing or suspending agents for aqueous suspensions include synthetic and natural gums such as tragacanth, acacia, alginate, dextran, sodium carboxymethyl cellulose, methylcellulose, polyvinyl-pyrrolidone or gelatin.

Preferred compositions for administration of a sigma receptor ligand or other therapeutic agent by injection include those comprising the therapeutic agent in association with a surface-active agent (or wetting agent or surfactant) or in the form of an emulsion (as a water-in-oil or oil-in-water emulsion).

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The therapeutic agent may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., eggs phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion will preferably comprise fat droplets between 0.1 and 1.0 $\mu$m, particularly 0.1 and 0.5 $\mu$m, and have a pH in the range of 5.5 to 8.0.

Compositions for inhalation or insufflation include solutions and suspensions in pharmaceutically acceptable, aqueous or organic solvents or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising devise may be attached to a face mask, tent or intermittent positive pressure breathing machine. Solution, suspension, or powder compositions may be administered, preferably orally or nasally, from devices which deliver the formulation in an appropriate manner.

Compositions of the present invention may also be presented for administration in the form of transdermal patches using conventional technology. The compositions may also be administered via the buccal cavity using, for example, absorption wafers.

The present invention further provides a process for the preparation of a pharmaceutical composition comprising a sigma receptor ligand and an SRI antidepressant agent, or pharmaceutically acceptable salts of the same, which process comprises bringing a sigma receptor ligand and the SRI antidepressant agent (or the pharmaceutically acceptable salts of one or both of these therapeutic agents) into association with a pharmaceutically acceptable carrier or excipient.

It will be appreciated that the amount of a sigma receptor ligand and the SRI antidepressant agent required for use in the treatment of depression will vary not only with the particular compounds or compositions selected but also with the route of administration, the nature of the condition being treated, and the age and condition of the patient, and will ultimately be at the discretion of the patient's physician or pharmacist.

The in vitro activity of the SRI antidepressant compounds used in this invention at the individual monoamine reuptake sites can be determined using rat synaptosomes or HEK-293 cells transfected with the human serotonin, dopamine or norepinephrine transporter, according to the following procedure adapted from those described by S. Snyder et al., (*Molecular Pharmacology*, 1971, 7, 66–80), D. T. Wong et al., (*Biochemical Pharmacology*, 1973, 22, 311–322), H. F. Bradford (*Journal of Neurochemistry*, 1969, 16, 675–684) and D. J. K. Balfour (*European Journal of Pharmacology*, 1973, 23, 19–26).

Synaptosomes: Male Sprague Dawley rats are decapitated and the brains rapidly removed. The cortex, hippocampi and corpus striata are dissected out and placed in ice cold sucrose buffer, 1 gram in 20 ml of buffer (the buffer is prepared using 320 mM sucrose containing 1 mg/ml glucose, 0.1 mM ethylenediamine tetraacetic acid (EDTA) adjusted to pH 7.4 with tris(hydroxymethyl)-aminomethane (TRIS) base). The tissues are homogenized in a glass homogenizing tube with a Teflon™ pestle at 350 rpm using a Potters homogenizer. The homogenate is centrifuged at 1000×g for 10 min. at 4° C. The resulting supernatant is recentrifuged at 17,000×g for 20 min. at 4° C. The final pellet is resuspended in an appropriate volume of sucrose buffer that yielded less than 10% uptake.

Cell Preparation: HEK-293 cells transfected with the human serotonin (5-HT), norepinephrine (NE) or dopamine (DA) transporter are grown in DMEM (Dulbecco's Modified Eagle Medium, Life Technologies Inc., 9800 Medical Center Dr., Gaithersburg, MD, catalog no. 11995-065)) supplemented with 10% dialyzed FBS (Fetal Bovine Serum, from Life Technologies, catalog no. 26300-053), 2 mM L-glutamine and 250 ug/ml G418 for the 5-HT and NE transporter or 2 ug/ml puromycin for the DA transporter, for selection pressure. The cells are grown in Gibco triple flasks, harvested with Phosphate Buffered Saline (Life Technologies, catalog no. 14190-136) and diluted to an appropriate amount to yield less than 10% uptake.

Neurotransmitter Uptake Assay: The uptake assays are conducted in glass tubes containing 50 uL of solvent, inhibitor or 10 uM sertraline, desipramine or nomifensine for the 5-HT, NE or DA assay nonspecific uptake, respectively. Each tube contains 400 uL of [3H]5-HT (5 nM final), [3H]NE (10 nM final) or [3H]DA (5 nM final) made up in modified Krebs solution containing 100 uM pargyline and glucose (1 mg/ml). The tubes are placed on ice and 50 uL of synaptosomes or cells is added to each tube. The tubes are then incubated at 37° C. for 7 min. (5-HT, DA) or 10 min. (NE). The incubation is terminated by filtration (GF/B filters), using a 96-well Brandel Cell Harvester, the filters are washed with modified Krebs buffer and counted using either a Wallac Model 1214 or Wallac Beta Plate Model 1205 scintillation counter.

Determination of the in vivo serotonin reuptake inhibition activity and potency of action for the compounds of the present invention can be made by measuring the ability of the compound to block the depletion of serotonin in the anterior cortex induced by (+/−)-para-chloroamphetamine (PCA) in the rat, according to a procedure adapted from R. W. Fuller, H. D. Snoddy and M. L. Cohen in *Neuropharmacology* 23: 539–544 (1984).

Generally, male, white Sprague-Dawley rats weighing 160–230 g each are assigned to either the control (vehicle) or test groups. When the test compound is administered subcutaneously (sc) at a given dose, it is co-administered with 5 mg/kg of para-chloroamphetamine (PCA). Three hours post-dose, the animals are sacrificed by decapitation and the anterior cortices are removed, wrapped in parafilm and frozen in dry ice (−78 C). When dosed orally (po), the rats are fasted the night before the experiment and then treated with the test compound at a given dose 30 minutes prior to the administration of the PCA (5 mg/kg, sc). After three hours, the animals are sacrificed and the tissues removed as above.

To determine the serotonin (5-HT) levels, the frozen tissues are homogenized with Branson sonifier in 0.5 mL of mobile phase in Eppendorf centrifuge tubes. Samples are then spun down at 11000 rpm for twenty minutes in a Sorval SH-MT rotor in a Sorval RC5C centrifuge. The supernatant thus obtained is pipetted into HPLC vials and the 5-HT levels are measured on HPLC-EC.

Interpretation of the results is as follows: Each experiment has a set of vehicle treated animals and a set of PCA-only animals. The mean 5-HT value of the PCA animals is subtracted from the mean 5-HT value of the vehicle animals. This is the signal or window of the response. The mean 5-HT value of each test group is determined, the mean of the PCA group subtracted from that, and that amount divided by the window is the per cent protection from the PCA effect for that dose. To report an $ID_{50}$, a line is drawn mathematically through the per cent protection values and the 50 per cent level calculated.

All of the title compounds of Formula I and II were assayed in vitro for serotonin, dopamine, and norepinephrine reuptake inhibition, and all had $IC_{50}$ values of about less than or equal to 250 nM for serotonin reuptake inhibition, about less than or equal to 1000 nM for dopamine reuptake inhibition, and about less than or equal to 1000 nM for norepinephrine reuptake inhibition.

When administered in combination, either as a single or as separate pharmaceutical composition(s), the sigma receptor ligand and an SRI antidepressant agent, are presented in a ratio which is consistent with the manifestation of the desired effect. In particular, the ratio by weight of the sigma receptor ligand and the SRI antidepressant agent will suitably be between 0.001 to 1 and 1000 to 1, and especially between 0.01 to 1 and 100 to 1.

As used herein the term "mammal" includes animals of economic importance such as bovine, ovine, and porcine animals, especially those that produce meat, as well as domestic animals (e.g. cats and dogs), sports animals (e.g. horses), zoo animals, and humans, the latter being preferred.

What is claimed is:

1. A pharmaceutical composition for the treatment of depression, in a mammal, comprising: (a) a compound that exhibits activity, respectively, as an SRI antidepressant, or a pharmaceutically acceptable salt thereof; (b) a sigma receptor ligand or pharmaceutically acceptable salt thereof; and (c) a pharmaceutically acceptable carrier; wherein the active agents "a" and "b" above are present in amounts that render the composition effective in treating, respectively, anxiety or refractory depression.

2. A pharmaceutical composition according to claim 1, wherein the SRI antidepressant or pharmaceutically acceptable salt thereof is selected from compounds of the formula I, and their pharmaceutically acceptable salts:

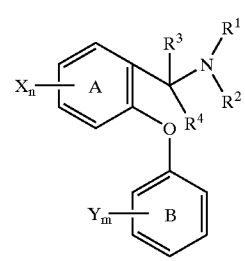

I wherein phenyl ring A and phenyl ring B can each, independently, be replaced by a naphthyl group, and wherein when phenyl ring A is replaced by a naphthyl group, the ethereal oxygen of structure I and the carbon to which $R^3$, $R^4$ and $NR^1R^2$ are attached, are attached to adjacent ring carbon atoms of the naphthyl group and neither of said adjacent ring carbon atoms is also adjacent to a fused ring carbon atom of said naphthyl group;

n and m are, selected, independently, from one, two and three;

R$^1$ and R$^2$ are selected, independently, from hydrogen (C$_1$–C$_4$)alkyl, (C$_2$–C$_4$)alkenyl, and (C$_2$–C$_4$)alkynyl, or R$^1$ and R$^2$, together with the nitrogen to which they are attached, form a four to eight membered saturated ring containing one or two heteroatoms, including the nitrogen to which R$^1$ and R$^2$ are attached, wherein the second heteroatom, when present, is selected from oxygen, nitrogen and sulfur, and wherein said ring may optionally be substituted at available binding sites with from one to three substituents selected, independently, from hydroxy and (C$_1$–C$_6$)alkyl;

R$^3$ and R$^4$ are selected, independently, from hydrogen and (C$_1$–C$_4$)alkyl optionally substituted with from one to three fluorine atoms, or R$^3$ and R$^4$, together with the carbon to which they are attached, form a four to eight membered saturated carbocyclic ring, and wherein said ring may optionally be substituted at available binding sites with from one to three substituents selected, independently, from hydroxy and (C$_1$–C$_6$)alkyl;

or R$^2$ and R$^3$, together with the nitrogen to which R$^2$ is attached and the carbon to which R$^3$ is attached, form a four to eight membered saturated ring containing one or two heteroatoms, including the nitrogen to which R$^2$ is attached, wherein the second heteroatom, when present, is selected from oxygen, nitrogen and sulfur, and wherein said ring may optionally be substituted at available binding sites with from one to three substituents selected, independently, from hydroxy and (C$_1$–C$_6$)alkyl;

each X and each Y is selected, independently, from hydrogen, halo (i.e., chloro, fluoro, bromo or iodo), (C$_1$–C$_4$)alkyl optionally substituted with from one to three fluorine atoms, (C$_1$–C$_4$)alkoxy optionally substituted with from one to three fluorine atoms, cyano, nitro, amino, (C$_{-C4}$)alkylamino, di-[(C$_1$–C$_4$)alkyl]amino, NR$^5$(C=O)(C$_1$–C$_4$)alkyl wherein R$^5$ is hydrogen or (C$_1$–C$_6$)alkyl, and SO$_p$(C$_1$–C$_6$)alkyl wherein p is zero, one or two; and with the proviso that: (a) no more than one of NR$^1$R$^2$, CR$^3$R$^4$ and R$^2$NCR$^3$ can form a ring; and (b) at least one X must be other than hydrogen when (i) R$^3$ and R$^4$ are both hydrogen, (ii) R$^1$ and R$^2$ are selected, independently, from hydrogen and (C$_1$–C$_4$)alkyl, and (iii) ring B is mono- or disubstituted with, respectively, one or two halo groups;

or a pharmaceutically acceptable salt thereof.

3. The composition of claim 2, wherein in the compound n is one, X is fluoro, R$^3$ and R$^4$ are hydrogen, R$^1$ is hydrogen, R$^2$ is methyl, m is two and Y is Y$_m$ is 3,4-dichloro.

4. The composition of claim 2, wherein in the compound m is zero, n is one, R$^3$ and R$^4$ are hydrogen, X is chloro, bromo, iodo or methyl, R$^1$ is hydrogen and R$^2$ is methyl.

5. The composition of claim 2, wherein the compound or salt is selected from the following:

[2-(3,4-Dichlorophenoxy)-5-fluorobenzyl]-dimethylamine;

[2-(3,4-Dichlorophenoxy)-5-fluorobenzyl]-methylamine;

[2-(3,4-Dichlorophenoxy)-5-trifluoromethylbenzyl]-dimethylamine;

N-[4-(3,4-Dichlorophenoxy)-3-dimethylaminomethylphenyl]-acetamide;

{1-[2-(3,4-Dichlorophenoxy)phenyl]-ethyl}-dimethylamine;

[2-(3,4-Dichlorophenoxy)-4-trifluoromethylbenzyl]-dimethylamine;

[2-(3,4-Dichlorophenoxy)-4-trifluoromethylbenzyl]-methylamine;

[4-Chloro-2-(3,4-dichlorophenoxy)-benzyl]-methylamine;

{1-[2-(3,4-Dichlorophenoxy)-5-fluorophenyl]-ethyl}-methylamine;

{1-[2-(3,4-Dichlorophenoxy)phenyl]-ethyl)}-methylamine;

{1-[2-(4-Chlorophenoxy)phenyl]ethyl}-methylamine;

[2-(3,4-Dichlorophenoxy)-5-methoxybenzyl]-methylamine;

[2-(4-Chlorophenoxy)-5-fluorobenzyl]-methylamine;

{1-[2-(4-Chlorophenoxy)-5-fluorophenyl]-ethyl}-methylamine;

[2-(3,4-Dichlorophenoxy)-5-methylbenzyl]-dimethylamine;

[4-Bromo-2-(3,4-dichlorophenoxy)-benzyl]-methylamine;

[5-Bromo-2-(3,4-dichlorophenoxy)-benzyl]-methylamine;

[2-(3,4-Dichlorophenoxy)-4,5-dimethoxybenzyl]-methylamine;

[2-(3,4-Dichlorophenoxy)-4-methoxybenzyl]-dimethylamine;

4-(3,4-Dichlorophenoxy)-4-methylaminomethyl-benzonitrile;

[2-(3,4-Dichlorophenoxy)-4,5-dimethylbenzyl]-methylamine;

3-(3,4-Dichlorphenoxy)-4-methylaminomethyl-benzonitrile;

(+)-{1-[2-(3,4-Dichlorophenoxy)-5-fluorophenyl]-ethyl}-methylamine;

(−)-{1-[2-(3,4-Dichlorophenoxy)-5-fluorophenyl]-ethyl}-methylamine;

[2-(3,4-Dichlorophenoxy)-5-trifluoromethyl-benzyl]-methylamine;

[2-(3,4-Dichlorophenoxy)-4-methoxybenzyl]-methylamine;

[2-(4-Chloro-3-fluorophenoxy)-5-fluorobenzyl]-methylamine;

[2-(3-Chloro-4-fluorophenoxy)-5-fluorobenzyl]-methylamine;

(+/−)2-[2-(3,4-Dichlorophenoxy)-5-fluorophenyl]-pyrrolidine;

(−)-2-[2-(3,4-Dichlorophenoxy)-5-fluorophenyl]-pyrrolidine;

(+)-2-[2-(3,4-Dichlorophenoxy)-5-fluorophenyl]-pyrrolidine;

2-[2-(3,4-Dichlorophenoxy)-5-fluorophenyl]-N-methylpyrrolidine;

{1-[2-(3,4-Dichlorophenoxy)-5-fluorophenyl]-1-methylethyl}-methylamine;

{1-[2-(3,4-Dichlorophenoxy)-5-fluorophenyl]-1-methylethyl}-dimethylamine;

[4-Chloro-2-(4-chlorophenoxy)-5-fluorobenzyl]-methylamine;

[2-(3,4-Dichlorophenoxy)-5-fluoro-4-methoxybenzyl]-methylamine;

[4-(3,4-Dichlorophenoxy)-3-(dimethylaminomethyl)-phenyl]-dimethylamine;

[5-Fluoro-2-(4-fluoro-3-methoxyphenoxy)-benzyl]-dimethylamine;

[2-(4-Chlorophenoxy)-5-isopropylbenzyl]-methylamine;

{1-[2-(4-Chlorophenoxy)-5-trifluoromethylphenyl]-ethyl}-methylamine;

[2-(4-Chlorophenoxy)-4,5-dimethylbenzyl]-methylamine;

{1-[5-Chloro-2(3,4-dichlorophenoxy)phenyl]-propyl}-methylamine;

[2-(3,4-Dichlorophenoxy)-5-methylsulfanyl-benzyl]-methylamine;

{1-[2-(3,4-Dichlorophenoxy)-5-methylsulfanyl-phenyl]-ethyl}-methylamine;

{1-[2-(3,4-Dichlorophenoxy)-5-methylsulfanyl-phenyl]-1-methylethyl}-methylamine;

[2-(3,4-Dichlorophenoxy)-5-methylsulfanyl-benzyl]-dimethylamine;

[2-(3,4-Dichlorophenoxy)-5-methanesulfinyl-benzyl]-dimethylamine;

[2-(3,4-Dichlorophenoxy)-5-methanesulfinyl-benzyl]-methylamine;

[2-(3,4-Dichlorophenoxy)-5-methanesulfonyl-benzyl]-methylamine;

[2-(3,4-Dichlorophenoxy)-5-methanesulfonyl-benzyl]-dimethylamine;

[2-(3,4-Dichlorophenoxy)-5(propane-2-sulfonyl)-benzyl]-methylamine;

2-[2-(3,4-Dichlorophenoxy)-5-fluorophenyl]-piperidine;

2-[2-(3,4-Dichlorophenoxy)-5-fluorophenyl]-1-methyl-piperidine;

3-[2-(3,4-Dichlorphenoxy)-5-fluorophenyl]-4-methyl-morpholine;

2-[2-(3,4-Dichlorophenoxy)-5-fluorophenyl]-1,2-dimethyl-piperidine;

{1-[2-(3,4-Dichlorophenoxy)-5-fluorophenyl]-cyclopropyl}-dimethylamine;

2-[2-(3,4-Dichlorophenoxy)-5-fluorophenyl]-1,5-dimethyl-pyrrolidine;

3-[2-(3,4-Dichlorophenoxy)-5-fluorophenyl]-4-methyl-thiomorpholine;

{1-[2-(3,4-Dichlorophenoxy)-5-fluorophenyl]-cyclopentyl}-methylamine;

{1-[2-(3,4-Dichlorophenoxy)-5-(propane-2-sulfonyl)-phenyl]-ethyl}-methylamine;

[4-Chloro-2-(3,4-dichlorophenoxy)-5-methanesulfonyl-benzyl]-methylamine;

and their pharmaceutically acceptable salts thereof.

6. A pharmaceutical composition according to claim 1, wherein the SRI antidepressant agent or pharmaceutically acceptable salt thereof is selected from compounds of the formula II, as defined below, and their pharmaceutically acceptable salts:

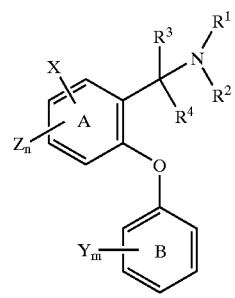

wherein phenyl ring A and phenyl ring B can each, independently, be replaced by a naphthyl group, and wherein when phenyl ring A is replaced by a naphthyl group, the ethereal oxygen of formula II and the carbon to which $R^3$, $R^4$ and $NR^1R^2$ are attached, are attached to adjacent ring carbon atoms of the naphthyl group and neither of said adjacent ring carbon atoms is also adjacent to a fused ring carbon atom of said naphthyl group;

n and m are, selected, independently, from one, two and three;

$R^1$ and $R^2$ are selected, independently, from hydrogen, $(C_1-C_4)$alkyl, $(C_2-C_4)$alkenyl, and $(C_2-C_4)$alkynyl, or $R^1$ and $R^2$, together with the nitrogen to which they are attached, form a four to eight membered saturated ring containing one or two heteroatoms, including the nitrogen to which $R^1$ and $R^2$ are attached, wherein the second heteroatom, when present, is selected from oxygen, nitrogen and sulfur, and wherein said ring may optionally be substituted at available binding sites with from one to three substituents selected, independently, from hydroxy and $(C_1-C_6)$alkyl;

$R^3$ and $R^4$ are selected, independently, from hydrogen and $(C_1-C_4)$alkyl optionally substituted with from one to three fluorine atoms, or $R^3$ and $R^4$, together with the carbon to which they are attached, form a four to eight membered saturated carbocyclic ring, and wherein said ring may optionally be substituted at available binding sites with from one to three substituents selected, independently, from hydroxy and $(C_1-C_6)$alkyl;

or $R^2$ and $R^3$, together with the nitrogen to which $R^2$ is attached and the carbon to which $R^3$ is attached, form a four to eight membered saturated ring containing one or two heteroatoms, including the nitrogen to which $R^2$ is attached, wherein the second heteroatom, when present, is selected from oxygen, nitrogen and sulfur, and wherein said ring may optionally be substituted at available binding sites with from one to three substituents selected, independently, from hydroxy and $(C_1-C_6)$alkyl;

each X is selected, independently, from phenyl, heteroaryl and heterocycle, and wherein each X may be further substituted by hydrogen, halo, $(C_1-C_4)$alkyl optionally substituted with from one to three fluorine atoms, $(C_1-C_4)$alkoxy optionally substituted with from one to three fluorine atoms, cyano, nitro, amino, hydroxy, carbonyl, $(C_1-C_4)$alkylamino, di-[$(C_1-C_4)$alkyl]amino, $NR^5(C=O)(C_1-C_4)$alkyl, $SO_2NR^5R^6$ and $SO_p(C_1-C_6)$alkyl, wherein $R^5$ and $R^6$ are selected, independently, from hydrogen and $(C_1-C_6)$alkyl, and p is zero, one or two;

each Y is selected, independently, from hydrogen, halo, $(C_1-C_4)$alkyl optionally substituted with from one to three fluorine atoms, $(C_1-C_4)$alkoxy optionally substituted with from one to three fluorine atoms, cyano, nitro, amino, $(C_1-C_4)$alkylamino, di-[$(C_1-C_4)$alkyl] amino, $NR^5(C=O)(C_1-C_4)$alkyl, $SO_2NR^5R^6$ and $SO_p(C_1-C_6)$alkyl, wherein $R^5$ and $R^6$ are selected, independently, from hydrogen and $(C_1-C_6)$alkyl, and p is zero, one or two; and each Z is selected independently from hydrogen, halo, $(C_1-C_4)$alkyl optionally substituted with from one to three fluorine atoms, $(C_1-C_4)$alkoxy;

or a pharmaceutically acceptable salt thereof.

7. The composition according to claim 6, wherein in the compound ring B is phenyl, not replaced with a naphthyl group.

8. The composition according to claim 6, wherein in the compound each Y is hydrogen or halo.

9. The composition according to claim 7, wherein in the compound m is 1 or 2, and wherein each Y is chlorine.

10. The composition according to claim 6, wherein in the compound X is selected from furan, thiophene, pyrrole, and 1,2,3-triazole, and wherein X may be further substituted.

11. The composition according to claim 6, wherein in the compound each Z is selected from hydrogen and halo.

12. The composition according to claim 11, wherein in the compound each Z is hydrogen.

13. The composition according to claim 6, wherein in the compound $R^3$ and $R^4$ are independently selected from hydrogen and unsubstituted $(C_1-C_4)$alkyl.

14. The composition according to claim 13, wherein in the compound one or both of $R^3$ and $R^4$ are hydrogen.

15. The composition according to claim 6, wherein in the compound $R^1$ and $R^2$ are independently selected from hydrogen and unsubstituted $(C_1-C_4)$alkyl.

16. The composition according to claim 15, wherein in the compound one of $R^1$ and $R^2$ is hydrogen and the other of $R^1$ and $R^2$ is $(C_1-C_4)$alkyl.

17. The composition according to claim 15, wherein in the compound one of $R^1$ and $R^2$ is hydrogen and the other of $R^1$ and $R^2$ is methyl.

18. The composition according to claim 6, wherein the compound is selected from the group consisting of:

[4-(3,4-Dichlorophenoxy)-biphenyl-3-ylmethyl]-methylamine;
[2-(3,4-Dichlorophenoxy)-5-thiophen-3-ylbenzyl]-methylamine;
[2-(3,4-Dichlorophenoxy)-4-thiophen-3-ylbenzyl]-methylamine;
[2-(3,4-Dichlorophenoxy)-4-furan-2-ylbenzyl]-methylamine;
[2-(3,4-Dichlorophenoxy)-5-furan-2-ylbenzyl]-methylamine;
N-[4'-(3,4-Dichlorphenoxy)-3'-methylaminomethyl-biphenyl-3-yl]-acetamide;
[2-(3,4-Dichlorophenoxy)-5-thiophen-2-ylbenzyl]-methylamine;
[4-(3,4-Dichlorophenoxy)-4'-fluoro-biphenyl-3-ylmethyl]-methylamine;
[2-(3,4-Dichlorophenoxy)-5-[1,2,3]triazol-1-ylbenzyl]-methylamine;
[2-(3,4-Dichlorophenoxy)-5-[1,2,3]triazol-2-ylbenzyl]-methylamine;
[2-(3,4-Dichlorophenoxy)-5-pyridin-2-ylbenzyl]-methylamine;
[2-(3,4-Dichlorophenoxy)-5-pyridin-3-ylbenzyl]-methylamine;
1-[4-(3,4-Dichlorophenoxy)-3-methylaminomethyl-phenyl]-1H-pyrazol-3-ylamine;
[2-(3,4-Dichlorophenoxy)-5-pyridin-4-ylbenzyl]-methylamine;
[3-(3,4-Dichlorophenoxy)-biphenyl-4-ylmethyl]-methylamine;
[4-(3,4-Dichlorophenoxy)-4'-methyl-biphenyl-3-ylmethyl]-methylamine;
[2-(3,4-Dichlorophenoxy)-4-thiophen-2-ylbenzyl]-methylamine;
[2-(3,4-Dichlorophenoxy)-5-pyrimidin-2-ylbenzyl]-methylamine;
[2-(3,4-Dichlorophenoxy)-5-pyrimidin-4-ylbenzyl]methyl amine;
[2-(3,4-Dichlorophenoxy)-5-(2-methylpyrimidin-4-yl)-benzyl]-methylamine;
{1-[2-(3,4-Dichlorophenoxy)-5-(2-methylpyrimidin-4-yl)-phenyl]-ethyl}-methylamine;
4-[4-(3,4-Dichlorophenoxy)-3-(1-methylpyrrolidin-2-yl)-phenyl]-2-methylpyrimidine;
[2-(4-Chlorophenoxy)-5-(1-methyl-1H-pyrrol-3-yl)-benzyl]-dimethylamine;
[5-(1-methyl-1H-pyrrol-3yl)-2-(naphthalen-2-yloxy)-benzyl]-dimethyl amine;
[5-Imidazol-1-yl-2-(naphthalen-2-yloxy)-benzyl]-dimethylamine;
1,5,5-Trimethyl-3-[3-methylaminomethyl-4-(naphthalen-2-yloxy)-phenyl]-imidazolidine-2,4-dione;
1-Methyl-3-[3-methylaminomethyl-4-(naphthalen-2-yloxy)-phenyl]-imidazolidine-2,4-dione;
3-[3-Methylaminomethyl-4-(naphthalen-2-yloxy)-phenyl]-thiazolidine-2,4-dione;
3-[3-Methylaminomethyl-4-(naphthalen-2-yloxy)-phenyl]-oxazolidine-2,4-dione;
3-[3-Methylaminomethyl-4-(naphthalen-2-yloxy)-phenyl]-oxazolidin-2-one;
3-[3-Methylaminomethyl-4-(naphthalen-2-yloxy)-phenyl]-thiazolidin-2-one;
1-Methyl-3-[3-methylaminomethyl-4-(naphthalen-2-yloxy)-phenyl]-imidazolidin-2-one:
1-Methyl-3-[3-methylaminomethyl-4-(naphthalen-2-yloxy)-phenyl]-tetrahydro-pyrimidin-2-one:
1-[4-(3,4-Dichlorophenoxy)-3-methylaminomethyl-phenyl]-3-methyl-tetrahydropyrimidin-2-one;
1-[4-(3,4-Dichlorophenoxy)-3-methylaminomethyl-phenyl]-3-methylimidazolidin-2-one;
3-[4-(3,4-Dichlorophenoxy)-3-methylaminomethyl-phenyl]-thiazolidin-2-one;
3-[4-(3,4-Dichlorophenoxy)-3-methylaminomethyl-phenyl]-oxazolidin-2-one;
[2-(3,4-Dichlorophenoxy)-5-(2-methylthiazol-4-yl)-benzyl]-methylamine;
[2-(3,4-Dichlorophenoxy)-5-(2-methyloxazol-4-yl)-benzyl]-methylamine;
[2-(3,4-Dichlorophenoxy)-5-(2,5-dimethyloxazol-4-yl)-benzyl]-methylamine;
[2-(3,4-Dichlorophenoxy)-5-(2,5-dimethylthiazol-4-yl)-benzyl]-methylamine;
[2-(3,4-Dichlorophenoxy)-5-(5-methyl-[1,2,4]thiadiazol-3-yl)-benzyl]-methylamine;
[2-(3,4-Dichlorophenoxy)-5-(5-methyl-[1,2,4]oxadiazol-3-yl)-benzyl]-methylamine;

[2-(3,4-Dichlorophenoxy)-5-[1,2,3]oxadiazol-4-yl-benzyl]-methylamine;
[2-(3,4-Dichlorophenoxy)-5-(5-methyl-[2,3]thiadiazol-4-yl)-benzyl]-methylamine;
[2-(3,4-Dichlorophenoxy)-5-(2,4-dimethyloxazol-5-yl)-benzyl]-methylamine;
[2-(3,4-Dichlorophenoxy)-5-(2,4-dimethylthiazol-5-yl)-benzyl]-methylamine;
[2-(3,4-Dichlorophenoxy)-5-[1,2,4]triazol-1-ylbenzyl]-methylamine;
[2-(3,4-Dichlorophenoxy)-5-(3-methyl-[1,2,4]triazol-1-yl)-benzyl]-methylamine;
[2-(4-Chlorophenoxy)-5-(3,5-dimethyl-[1,2,4]triazol-1-yl)-benzyl]-methylamine;
[2-(4-Chlorophenoxy)-5-tetrazol-1-ylbenzyl]-methylamine;
[2-(4-Chlorophenoxy)-5-(5-methyltetrazol-1-yl)-benzyl]-dimethylamine;
[2-(4-Chlorophenoxy)-5-[1,2,4]triazol-4-ylbenzyl]-dimethylamine;
[2-(4-Chlorophenoxy)-5-(1-methyl-1H-tetrazol-5-yl)-benzyl]-dimethylamine;
{1-[2-(3,4-Dichlorophenoxy)-5-(1-methyl-1H-tetrazol-5-yl)-phenyl]-ethyl}-dimethylamine, and their pharmaceutically acceptable salts thereof.

19. A pharmaceutical composition according to claim 1 wherein the sigma receptor ligand or a pharmaceutically acceptable salt thereof is selected from:
igmesine [N-(1,4-diphenyl-1-ethyl-3-buten-1-yl)-N-methyl-cyclopropanemethanamine hydrochloride];
siramesine [1'-(4-(1-(4-fluorophenyl)-1H-indol-3-yl)-1-butyl)-spiro(isobenzofuran-1(3H), 4'-piperidine];
E-5842 [4-(4-fluorophenyl)-1,2,3,6-tetrahydro-1-(4-(2H-1,2,4-triazol-1-yl)butylpyridine];
MS-377 [(R)-1-(4-chlorophenyl)-3-[4-(2-methoxyethyl)-piperazin-1-yl]methyl-2-pyrrolidinone];
NE-100 [N,N-dipropyl-2-[4-methoxy-3-(2-phenylethoxy)phenyl]ethylamine];
OPC-14523 [1-(3-(4-(3-chlorophenyl)-1-piperazinyl)propyl)-5-methoxy-3,4-dihydro-2-quinolinone];
SA-4503 [1-(3,4-dimethoxyphenethyl)-4-(3-phenylpropyl)-Piperazine];
SR-31742A [(Z)-1-(3-(3-chloro-4-cyclohexylphenyl)-2-propenyl)-hexahydro-1H-azepine];
haloperidol [4-[4-(4-chlorophenyl)-4-hydroxy-1-piperidinyl]-1-(4-fluorophenyl)-1-butanone];
cis-7-(cyclopentanespiro-3'-glutaramidomethyl)-2-(2-phenethyl)-perhydro-1H-pyrido[1,2a]pyrazine;
SKF-10,047 [2S-(2α, 6α),11R]-1,2,3,4,5,6-hexahydro-6,11-dimethyl-3-(2-propenyl)-2,6-methano-3-benzazocin-8-ol];
Dextromethorphan](+)-3-methoxy-17-methyl-9α,13α,14α-morphinan]; and
BMY-14802 [α-(4-fluorophenyl)-4-(5-fluoro-2-pyrimidinyl)-1-piperazinebutanol monohydrochloride].

20. A pharmaceutical composition according to claim 1 wherein the amount of the SRI antidepressant, or pharmaceutically acceptable salt thereof, in said composition is from about 0.05 mg to about 1500 mg and the amount of the sigma receptor ligand or pharmaceutically acceptable salt thereof is from about 0.5 mg to about 1500 mg.

21. A pharmaceutical composition according to claim 20 wherein the amount of the SRI antidepressant, or pharmaceutically acceptable salt thereof, in said composition is from about 2.5 mg to about 500 mg and the amount of the sigma receptor ligand or pharmaceutically acceptable salt thereof is from about 5 mg to about 200 mg.

22. A method of treating depression, in a mammal, comprising administering to said mammal: (a) a compound that exhibits activity as an SRI antidepressant, or a pharmaceutically acceptable salt thereof; and (b) a sigma receptor ligand or pharmaceutically acceptable salt thereof, wherein the active agents "a" and "b" above are present in amounts that render the combination of the two agents effective in treating, respectively, anxiety or refractory depression.

23. A method according to claim 22, wherein the SRI antidepressant or pharmaceutically acceptable salt thereof is selected from compounds of the formula I,

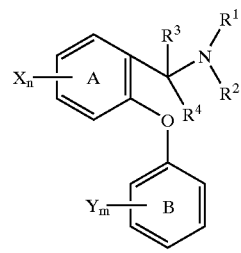

I wherein phenyl ring A and phenyl ring B can each, independently, be replaced by a naphthyl group, and wherein when phenyl ring A is replaced by a naphthyl group, the ethereal oxygen of structure I and the carbon to which $R^3$, $R^4$ and $NR^1R^2$ are attached, are attached to adjacent ring carbon atoms of the naphthyl group and neither of said adjacent ring carbon atoms is also adjacent to a fused ring carbon atom of said naphthyl group;

n and m are, selected, independently, from one, two and three;

$R^1$ and $R^2$ are selected, independently, from hydrogen ($C_1$–$C_4$)alkyl, ($C_2$–$C_4$)alkenyl, and ($C_2$–$C_4$)alkynyl, or $R^1$ and $R^2$, together with the nitrogen to which they are attached, form a four to eight membered saturated ring containing one or two heteroatoms, including the nitrogen to which $R^1$ and $R^2$ are attached, wherein the second heteroatom, when present, is selected from oxygen, nitrogen and sulfur, and wherein said ring may optionally be substituted at available binding sites with from one to three substituents selected, independently, from hydroxy and ($C_1$–$C_6$)alkyl;

$R^3$ and $R^4$ are selected, independently, from hydrogen and ($C_1$–$C_4$)alkyl optionally substituted with from one to three fluorine atoms, or $R^3$ and $R^4$, together with the carbon to which they are attached, form a four to eight membered saturated carbocyclic ring, and wherein said ring may optionally be substituted at available binding sites with from one to three substituents selected, independently, from hydroxy and ($C_1$–$C_6$)alkyl;

or $R^2$ and $R^3$, together with the nitrogen to which $R^2$ is attached and the carbon to which $R^3$ is attached, form a four to eight membered saturated ring containing one or two heteroatoms, including the nitrogen to which $R^2$ is attached, wherein the second heteroatom, when present, is selected from oxygen, nitrogen and sulfur, and wherein said ring may optionally be substituted at available binding sites with from one to three substituents selected, independently, from hydroxy and ($C_1$–$C_6$)alkyl;

each X and each Y is selected, independently, from hydrogen, halo (i.e., chloro, fluoro, bromo or iodo), $(C_1-C_4)$alkyl optionally substituted with from one to three fluorine atoms, $(C_1-C_4)$alkoxy optionally substituted with from one to three fluorine atoms, cyano, nitro, amino, $(C_{-C4})$alkylamino, di-$[(C_1-C_4)$alkyl]amino, $NR^5(C=O)(C_1-C_4)$alkyl wherein $R^5$ is hydrogen or $(C_1-C_6)$alkyl, and $SO_p(C_1-C_6)$alkyl wherein p is zero, one or two; and with the proviso that: (a) no more than one of $NR^1R^2$, $CR^3R^4$ and $R^2NCR^3$ can form a ring; and (b) at least one X must be other than hydrogen when (i) $R^3$ and $R^4$ are both hydrogen, (ii) $R^1$ and $R^2$ are selected, independently, from hydrogen and $(C_1-C_4)$alkyl, and (iii) ring B is mono- or disubstituted with, respectively, one or two halo groups;

or a pharmaceutically acceptable salt thereof.

24. A method according to claim 22, wherein the SRI antidepressant or pharmaceutically acceptable salt thereof is selected from compounds of the formula II,

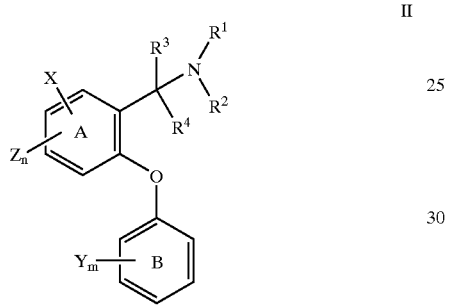

II wherein phenyl ring A and phenyl ring B can each, independently, be replaced by a naphthyl group, and wherein when phenyl ring A is replaced by a naphthyl group, the ethereal oxygen of structure I and the carbon to which $R^3$, $R^4$ and $NR^1R^2$ are attached, are attached to adjacent ring carbon atoms of the naphthyl group and neither of said adjacent ring carbon atoms is also adjacent to a fused ring carbon atom of said naphthyl group;

n and m are, selected, independently, from one, two and three;

$R^1$ and $R^2$ are selected, independently, from hydrogen, $(C_1-C_4)$alkyl, $(C_2-C_4)$alkenyl, and $(C_2-C_4)$alkynyl, or $R^1$ and $R^2$, together with the nitrogen to which they are attached, form a four to eight membered saturated ring containing one or two heteroatoms, including the nitrogen to which $R^1$ and $R^2$ are attached, wherein the second heteroatom, when present, is selected from oxygen, nitrogen and sulfur, and wherein said ring may optionally be substituted at available binding sites with from one to three substituents selected, independently, from hydroxy and $(C_1-C_6)$alkyl;

$R^3$ and $R^4$ are selected, independently, from hydrogen and $(C_1-C_4)$alkyl optionally substituted with from one to three fluorine atoms, or $R^3$ and $R^4$ together with the carbon to which they are attached, form a four to eight membered saturated carbocyclic ring, and wherein said ring may optionally be substituted at available binding sites with from one to three substituents selected, independently, from hydroxy and $(C_1-C_6)$alkyl;

or $R^2$ and $R^3$, together with the nitrogen to which $R^2$ is attached and the carbon to which $R^3$ is attached, form a four to eight membered saturated ring containing one or two heteroatoms, including the nitrogen to which $R^2$ is attached, wherein the second heteroatom, when present, is selected from oxygen, nitrogen and sulfur, and wherein said ring may optionally be substituted at available binding sites with from one to three substituents selected, independently, from hydroxy and $(C_1-C_6)$alkyl;

each X is selected, independently, from phenyl, heteroaryl and heterocycle, and wherein each X may be further substituted by hydrogen, halo, $(C_1-C_4)$alkyl optionally substituted with from one to three fluorine atoms, $(C_1-C_4)$alkoxy optionally substituted with from one to three fluorine atoms, cyano, nitro, amino, hydroxy, carbonyl, $(C_1-C_4)$alkylamino, di-$[(C_1-C_4)$alkyl]amino, $NR^5(C=O)(C_1-C_4)$alkyl, $SO_2NR^5R^6$ and $SO_p(C_1-C_6)$ alkyl, wherein $R^5$ and $R^6$ are selected, independently, from hydrogen and $(C_1-C_6)$alkyl, and p is zero, one or two;

each Y is selected, independently, from hydrogen, halo, $(C_1-C_4)$alkyl optionally substituted with from one to three fluorine atoms, $(C_1-C_4)$alkoxy optionally substituted with from one to three fluorine atoms, cyano, nitro, amino, $(C_1-C_4)$alkylamino, di-$[(C_1-C_4)$alkyl] amino, $NR^6(C=O)(C_1-C_4)$alkyl, $SO_2NR^5R^6$ and $SO_p(C_1-C_6)$alkyl, wherein $R^5$ and $R^6$ are selected, independently, from hydrogen and $(C_1-C_6)$alkyl, and p is zero, one or two; and each Z is selected independently from hydrogen, halo, $(C_1-C_4)$alkyl optionally substituted with from one to three fluorine atoms, $(C_1-C_4)$alkoxy;

or a pharmaceutically acceptable salt thereof.

25. A method according to claim 22, wherein the (SRI) antidepressant, or pharmaceutically acceptable salt thereof, and the sigma receptor ligand or pharmaceutically acceptable salt thereof, are administered as part of the same dosage form.

26. A method according to claim 22, wherein the sigma receptor ligand, or pharmaceutically acceptable salt thereof, is administered in an amount from about 0.5 mg per day to about 1500 mg per day, and the antidepressant, or pharmaceutically acceptable salt thereof, is administered in an amount from about 0.05 mg per day to about 1500 mg per day.

27. A method according to claim 26, wherein the sigma receptor ligand is administered in an amount ranging from about 5 mg per day to about 200 mg per day and the antidepressant or pharmaceutically acceptable salt thereof, is administered from about 2.5 mg per day to about 500 mg per day.

28. A method according to claim 22, wherein the sigma receptor ligand or pharmaceutically acceptable salt thereof is selected from:

igmesine [N-(1,4-diphenyl-1-ethyl-3-buten-1-yl)-N-methyl-cyclopropanemethanamine hydrochloride];

siramesine [1'-(4-(1-(4-fluorophenyl)-1H-indol-3-yl)-1-butyl)-spiro(isobenzofuran-1(3H), 4'-piperidine];

E-5842 [4-(4-fluorophenyl)-1,2,3,6-tetrahydro-1-(4-(2H-1,2,4-triazol-1-yl)butylpyridine];

MS-377 [(R)-1-(4-chlorophenyl)-3-[4-(2-methoxyethyl)-piperazin-1-yl]methyl-2-pyrrolidinone];

NE-100 [N,N-dipropyl-2-[4-methoxy-3-(2-phenylethoxy)phenyl]ethylamine];

OPC-14523 [1-(3-(4-(3-chlorophenyl)-1-piperazinyl) propyl)-5-methoxy-3,4-dihydro-2-quinolinone];

SA-4503 [1-(3,4-dimethoxyphenethyl)-4-(3-phenylpropyl)-piperazine];

SR-31742A [(Z)-1-(3-(3-chloro-4-cyclohexylphenyl)-2-propenyl)-hexahydro-1H-azepine];

haloperidol [4-[4-(4-chlorophenyl)-4-hydroxy-1-piperidinyl]-1-(4-fluorophenyl)-1-butanone];

cis-7-(cyclopentanespiro-3'-glutaramidomethyl)-2-(2-phenethyl)-perhydro-1H-pyrido[1,2a]pyrazine;

SKF-10,047 [2S-(2α, 6α),11R]-1,2,3,4,5,6-hexahydro-6,11-dimethyl-3-(2-propenyl)-2,6-methano-3-benzazocin-8-ol];

Dextromethorphan [(+)-3-methoxy-17-methyl-9α,13α,14α-morphinan]; and

BMY-14802 [α-(4-fluorophenyl)-4-(5-fluoro-2-pyrimidinyl)-1-piperazinebutanol monohydrochloride].

29. A method according to claim 23, wherein the SRI antidepressant agent or pharmaceutically acceptable salt thereof that is employed in such composition is selected from the following compounds and their pharmaceutically acceptable salts:

[4-(3,4-Dichlorophenoxy)-biphenyl-3-ylmethyl]-methylamine;

[2-(3,4-Dichlorophenoxy)-5-thiophen-3-ylbenzyl]-methylamine;

[2-(3,4-Dichlorophenoxy)-4-thiophen-3-ylbenzyl]-methylamine;

[2-(3,4-Dichlorophenoxy)-4-furan-2-ylbenzyl]-methylamine;

[2-(3,4-Dichlorophenoxy)-5-furan-2-ylbenzyl]-methylamine;

N-[4'-(3,4-Dichlorphenoxy)-3'-methylaminomethyl-biphenyl-3-yl]-acetamide;

[2-(3,4-Dichlorophenoxy)-5-thiophen-2-ylbenzyl]-methylamine;

[4-(3,4-Dichlorophenoxy)-4'-fluoro-biphenyl-3-ylmethyl]-methylamine;

[2-(3,4-Dichlorophenoxy)-5-[1,2,3]triazol-1-ylbenzyl]-methylamine;

[2-(3,4-Dichlorophenoxy)-5-[1,2,3]triazol-2-ylbenzyl]-methylamine;

[2-(3,4-Dichlorophenoxy)-5-pyridin-2-ylbenzyl]-methylamine;

[2-(3,4-Dichlorophenoxy)-5-pyridin-3-ylbenzyl]-methylamine;

[4-(3,4-Dichlorophenoxy)-3-methylaminomethylphenyl]-1H-pyrazol-3-ylamine;

[2-(3,4-Dichlorophenoxy)-5-pyridin-4-ylbenzyl]-methylamine;

[3-(3,4-Dichlorophenoxy)-biphenyl-4-ylmethyl]-methylamine;

[4-(3,4-Dichlorophenoxy)-4'-methyl-biphenyl-3-ylmethyl]-methylamine;

[2-(3,4-Dichlorophenoxy)-4-thiophen-2-ylbenzyl]-methylamine;

[2-(3,4-Dichlorophenoxy)-5-pyrimidin-2-ylbenzyl]-methylamine;

[2-(3,4-Dichlorophenoxy)-5-pyrimidin-4-ylbenzyl]-methylamine;

[2-(3,4-Dichlorophenoxy)-5-(2-methylpyrimidin-4-yl)-benzyl]-methylamine;

{1-[2-(3,4-Dichlorophenoxy)-5-(2-methylpyrimidin-4-yl)-phenzyl]-ethyl}-methylamine;

4-[4-(3,4-Dichlorophenoxy)-3-(1-methylpyrrolidin-2-yl)-phenyl]-2-methylpyrimidine;

[2-(4-Chlorophenoxy)-5-(1-methyl-1H-pyrrol-3-yl)-benzyl]-dimethylamine;

[5-(1-methyl-1H-pyrrol-3-yl)-2-(naphthalen-2-yloxy)-benzyl]-dimethyl amine;

[5-Imidazol-1-yl-2-(naphthalen-2-yloxy)-benzyl]-dimethylamine;

1,5,5-Trimethyl-3-[3-methylaminomethyl-4-(naphthalen-2-yloxy)-phenyl]-imidazolidine-2,4-dione;

1-Methyl-3-[3-methylaminomethyl-4-(naphthalen-2-yloxy)-phenyl]-imidazolidine-2,4-dione;

3-[3-Methylaminomethyl-4-(naphthalen-2-yloxy)-phenyl]-thiazolidine-2,4-dione;

3-[3-Methylaminomethyl-4-(naphthalen-2-yloxy)-phenyl]-oxazolidine-2,4-dione;

3-[3-Methylaminomethyl-4-(naphthalen-2-yloxy)-phenyl]-oxazolidin-2-one;

3-[3-Methylaminomethyl-4-(naphthalen-2-yloxy)-phenyl]-thiazolidin-2-one;

1-Methyl-3-[3-methylaminomethyl-4-(naphthalen-2-yloxy)-phenyl]-imidazolidin-2-one;

1-Methyl-3-[3-methylaminomethyl-4-(naphthalen-2-yloxy)-phenyl]-tetrahydro-pyrimidin-2-one;

1-[4-(3,4-Dichlorophenoxy)-3-methylaminomethyl-phenyl]-3-methyl-tetrahydro-pyrimidin-2-one;

1-[4-(3,4-Dichlorophenoxy)-3-methylaminomethyl-phenyl]-3-methylimidazolidin-2-one;

3-[4-(3,4-Dichlorophenoxy)-3-methylaminomethyl-phenyl]-thiazolidin-2-one;

3-[4-(3,4-Dichlorophenoxy)-3-methylaminomethyl-phenyl]-oxazolidin-2-one;

[2-(3,4-Dichlorophenoxy)-5-(2-methylthiazol-4-yl)-benzyl]-methylamine;

[2-(3,4-Dichlorophenoxy)-5-(2-methyloxazol-4-yl)-benzyl]-methylamine;

[2-(3,4-Dichlorophenoxy)-5-(2,5-dimethyloxazol-4-yl)-benzyl]-methylamine;

[2-(3,4-Dichlorophenoxy)-5-(2,5-dimethylthiazol-4-yl)-benzyl]-methylamine;

[2-(3,4-Dichlorophenoxy)-5-(5-methyl-[1,2,4]thiadiazol-3-yl)-benzyl]-methylamine;

[2-(3,4-Dichlorophenoxy)-5-(5-methyl-[1,2,4]oxadiazol-3-yl)-benzyl]-methylamine;

[2-(3,4-Dichlorophenoxy)-5-[1,2,3]oxadiazol-4-yl-benzyl]-methylamine;

[2-(3,4-Dichlorophenoxy)-5-(5-methyl-[1,2,3]thiadiazol-4-yl)-benzyl]-methylamine;

[2-(3,4-Dichlorophenoxy)-5-(2,4-dimethyloxazol-5-yl)-benzyl]-methylamine;

[2-(3,4-Dichlorophenoxy)-5-(2,4-dimethylthiazol-5-yl)-benzyl]-methylamine;

[2-(3,4-Dichlorophenoxy)-5-[1,2,4]triazol-1-ylbenzyl]-methylamine;

[2-(3,4-Dichlorophenoxy)-5-(3-methyl-[1,2,4]triazol-1-yl)-benzyl]-methylamine;

[2-(4-Chlorophenoxy)-5-(3,5-dimethyl-[1,2,4]triazol-1-yl)-benzyl]-methylamine;

[2-(4-Chlorophenoxy)-5-tetrazol-1-ylbenzyl]-methylamine;

[2-(4-Chlorophenoxy)-5-(5-methyltetrazol-1-yl)-benzyl]-dimethylamine;

[2-(4-Chlorophenoxy)-5-[1,2,4]triazol-4-ylbenzyl]-dimethylamine;

[2-(4-Chlorophenoxy)-5-(1-methyl-1H-tetrazol-5-yl)-benzyl]-dimethylamine; and

{1-[2-(3,4-Dichlorophenoxy)-5-(1-methyl-1H-tetrazol-5-yl)-phenyl]-ethyl}-dimethylamine.

30. A method according to claim 24, wherein the SRI antidepressant or pharmaceutically acceptable salt thereof that is employed in such method is selected from the following compounds and their pharmaceutically acceptable salts:

[2-(3,4-Dichlorophenoxy)-5-fluorobenzyl]-dimethylamine;
[2-(3,4-Dichlorophenoxy)-5-fluorobenzyl]-methylamine;
[2-(3,4-Dichlorophenoxy)-5-trifluoromethylbenzyl]-dimethylamine;
N-[4-(3,4-Dichlorophenoxy)-3-dimethylaminomethylphenyl]-acetamide;
1-[2-(3,4-Dichlorophenoxy)phenyl]-ethyl}-dimethylamine;
[2-(3,4-Dichlorophenoxy)-4-trifluoromethylbenzyl]-dimethylamine;
[2-(3,4-Dichlorophenoxy)-4-trifluoromethylbenzyl]-methylamine;
[4-Chloro-2-(3,4-dichlorophenoxy)-benzyl]-methylamine;
{1-[2-(3,4-Dichlorophenoxy)-5-fluorophenyl]-ethyl}-methylamine;
{1-[2-(3,4-Dichlorophenoxy)phenyl]-ethyl}-methylamine;
{1-[2-(4-Chlorophenoxy)phenyl]ethyl}-methylamine;
[2-(3,4-Dichlorophenoxy)-5-methoxybenzyl]-methylamine;
[2-(4-Chlorophenoxy)-5-fluorobenzyl]-methylamine; and
{1-[2-(4-Chlorophenoxy)-5-fluorophenyl]-ethyl}-methylamine;
[2-(3,4-Dichlorophenoxy)-5-methylbenzyl]-dimethylamine;
[4-Bromo-2-(3,4-dichlorophenoxy)-benzyl]-methylamine;
[5-Bromo-2-(3,4-dichlorophenoxy)-benzyl]-methylamine;
[2-(3,4-Dichlorophenoxy)-4,5-dimethoxybenzyl]-methylamine;
[2-(3,4-Dichlorophenoxy)-4-methoxybenzyl]-dimethylamine;
4-(3,4-Dichlorophenoxy)-3-methylaminomethyl-benzonitrile;
[2-(3,4-Dichlorophenoxy)-4,5-dimethylbenzyl]-methylamine;
3-(3,4-Dichlorphenoxy)-4-methylaminomethyl-benzonitrile;
(+)-{1-[2-(3,4-Dichlorophenoxy)-5-fluorophenyl]-ethyl}-methylamine;
(−)-{1-[2-(3,4-Dichlorophenoxy)-5-fluorophenyl]-ethyl}-methylamine;
[2-(3,4-Dichlorophenoxy)-5-trifluoromethyl-benzyl]-methylamine;
[2-(3,4-Dichlorophenoxy)-4-methoxybenzyl]-methylamine;
[2-(4-Chloro-3-fluorophenoxy)-5-fluorobenzyl]-methylamine;
[2-(3-Chloro-4-fluorophenoxy)-5-fluorobenzyl]-methylamine;
(+/−)-2-[2-(3,4-Dichlorophenoxy)-5-fluorophenyl]-pyrrolidine;
(−)-2-[2-(3,4-Dichlorophenoxy)-5-fluorophenyl]-pyrrolidine;
(+)-2-[2-(3,4-Dichlorophenoxy)-5-fluorophenyl]-pyrrolidine;
2-[2-(3,4-Dichlorophenoxy)-5-fluorophenyl]-N-methylpyrrolidine;
{A -[2-(3,4-Dichlorophenoxy)-5-fluorophenyl]-1-methylethyl}-methylamine;
{1-[2-(3,4-Dichlorophenoxy)-5-fluorophenyl]-1-methylethyl}-dimethylamine;
[4-Chloro-2-(4-chlorophenoxy)-5-fluorobenzyl]-methylamine;
[2-(3,4-Dichlorophenoxy)-5-fluoro-4-methoxybenzyl]-methylamine;
[4-(3,4-Dichlorophenoxy)-3-(dimethylaminomethyl)-phenyl]-dimethylamine
[5-Fluoro-2-(4-fluoro-3-methoxyphenoxy)-benzyl]-dimethylamine;
[2-(4-Chlorophenoxy)-5-isopropylbenzyl]-methylamine;
{1-[2-(4-Chlorophenoxy)-5-trifluoromethylphenyl]-ethyl}-methylamine;
[2-(4-Chlorophenoxy)-4,5-dimethylbenzyl]-methylamine;
{1-[5-Chloro-2(3,4-dichlorophenoxy)phenyl]-propyl}-methylamine;
[2-(3,4-Dichlorophenoxy)-5-methylsulfanyl-benzyl]-methylamine;
{1-[2-(3,4-Dichlorophenoxy)-5-methylsulfanyl-phenyl]-ethyl}-methylamine;
{1-[2-(3,4-Dichloro-phenoxy)-5-methylsulfanyl-phenyl]-1-methylethyl}-methylamine;
[2-(3,4-Dichlorophenoxy)-5-methylsulfanyl-benzyl]-dimethylamine;
[2-(3,4-Dichlorophenoxy)-5-methanesulfinyl-benzyl]-dimethylamine;
[2-(3,4-Dichlorophenoxy)-5-methanesulfinyl-benzyl]-methylamine;
[2-(3,4-Dichlorophenoxy)-5-methanesulfonyl-benzyl]-methylamine;
[2-(3,4-Dichlorophenoxy)-5-methanesulfonyl-benzyl]-dimethylamine;
[2-(3,4-Dichlorophenoxy)-5-(propane-2-sulfonyl)-benzyl]-methylamine;
2-[2-(3,4-Dichlorophenoxy)-5-fluorophenyl]-piperidine;
2-[2-(3,4-Dichlorophenoxy)-5-fluorophenyl]-1-methyl-piperidine;
3-[2-(3,4-Dichlorophenoxy)-5-fluorophenyl]-4-methyl-morpholine;
2-[2-(3,4-Dichlorophenoxy)-5-fluorophenyl]-1,2-dimethyl-piperidine;
{1-[2-(3,4-Dichlorophenoxy)-5-fluorophenyl]-cyclopropyl}-dimethylamine;
2-[2-(3,4-Dichlorophenoxy)-5-fluorophenyl]-1,5-dimethyl-pyrrolidine;
3-[2-(3,4-Dichlorophenoxy)-5-fluorophenyl]-4-methyl-thiomorpholine;
{1-[2-(3,4-Dichlorophenoxy)-5-fluorophenyl]-cyclopentyl}-methylamine;
{1-[2-(3,4-Dichlorophenoxy)-5-(propane-2-sulfonyl)-phenyl]-ethyl}-methylamine; and
[4-Chloro-2-(3,4-dichlorophenoxy)-5-methanesulfonyl-benzyl]-methylamine.

* * * * *